(12) United States Patent
Remarchuk et al.

(10) Patent No.: US 11,427,571 B2
(45) Date of Patent: *Aug. 30, 2022

(54) POLYMORPHS AND SOLID FORMS OF A PYRIMIDINYLAMINO-PYRAZOLE COMPOUND, AND METHODS OF PRODUCTION

(71) Applicant: DENALI THERAPEUTICS INC., South San Francisco, CA (US)

(72) Inventors: Travis Remarchuk, South San Francisco, CA (US); Anantha Sudhakar, South San Francisco, CA (US)

(73) Assignee: DENALI THERAPEUTICS INC.

( * ) Notice: Subject to any disclaimer, the term of this patent is extended or adjusted under 35 U.S.C. 154(b) by 0 days.

This patent is subject to a terminal disclaimer.

(21) Appl. No.: 17/105,870

(22) Filed: Nov. 27, 2020

(65) Prior Publication Data

US 2021/0087176 A1 Mar. 25, 2021

Related U.S. Application Data

(63) Continuation of application No. 16/447,713, filed on Jun. 20, 2019, now Pat. No. 10,851,088, which is a continuation of application No. 16/197,037, filed on Nov. 20, 2018, now Pat. No. 10,370,361.

(60) Provisional application No. 62/589,276, filed on Nov. 21, 2017.

(51) Int. Cl.
*C07D 403/12* (2006.01)
*A61P 25/28* (2006.01)
*A61K 9/20* (2006.01)

(52) U.S. Cl.
CPC ............. *C07D 403/12* (2013.01); *A61K 9/20* (2013.01); *A61P 25/28* (2018.01); *C07B 2200/13* (2013.01)

(58) Field of Classification Search
CPC .................................................. C07D 403/12
USPC ....................................................... 544/324
See application file for complete search history.

(56) References Cited

U.S. PATENT DOCUMENTS

| | | | |
|---|---|---|---|
| 8,354,420 B2 | 1/2013 | Baker-Glenn et al. | |
| 8,569,281 B2 | 10/2013 | Chan et al. | |
| 8,791,130 B2 | 7/2014 | Baker-Glenn et al. | |
| 8,796,296 B2 | 8/2014 | Baker-Glenn et al. | |
| 8,802,674 B2 | 8/2014 | Baker-Glenn et al. | |
| 8,809,331 B2 | 8/2014 | Baker-Glenn et al. | |
| 8,815,882 B2 | 8/2014 | Baker-Glenn et al. | |
| 9,145,402 B2 | 9/2015 | Baker-Glenn et al. | |
| 9,212,173 B2 | 12/2015 | Baker-Glenn et al. | |
| 9,212,186 B2 | 12/2015 | Baker-Glenn et al. | |
| 9,932,325 B2 | 4/2018 | Estrada et al. | |
| 10,370,361 B2 * | 8/2019 | Remarchuk | C07D 403/12 |
| 10,851,088 B2 * | 12/2020 | Remarchuk | C07D 403/12 |
| 2012/0157427 A1 | 6/2012 | Baker-Glenn et al. | |
| 2015/0051238 A1 | 2/2015 | Baker-Glenn et al. | |
| 2015/0250790 A1 | 9/2015 | Parikh et al. | |
| 2017/0362206 A1 | 12/2017 | Estrada et al. | |
| 2019/0194170 A1 | 6/2019 | Remarchuk et al. | |

FOREIGN PATENT DOCUMENTS

| | | |
|---|---|---|
| CL | 2012003229 A1 | 1/2013 |
| CL | 2018003597 A1 | 2/2019 |
| WO | 2012062783 | 5/2012 |

OTHER PUBLICATIONS

Supplementary European Search Report in EP 18881859.5 dated Jun. 7, 2021, 7 pages.
Communication pursuant to Rules 70(2) and 70a(2) EPC in EP 18881859.5 dated Jun. 24, 2021, 1 page.
Chan, B., et al., "Discovery of a Highly Selective, Brain-Penetrant Aminopyrazole LRRK2 Inhibitor," ACS Med Chem Lett 4, 85-90 (2013).
Chen, H. et al., "Discovery of Selective LRRK2 Inhibitors Guided by Computational Analysis and Molecular Modeling," J. Med Chem 55, 5536-5545 (2012).
Christensen, K., et al., "Development of LRRK2 Inhibitors for the Treatment of Parkinson's Disease," Progress in Medicinal Chemistry 56, 37-80 (2017).
Estrada, A., et al., "Chemcial Biology of Leucine-Rich Repeat Kinase 2 (LRRK2) Inhibitors," J Med Chem 58, 5733-6746 (2015).
Estrada, A., et al., "Discovery of Highly Potent, Selective, and Brain-Penetrant Aminopyrazole Leucine-Rich Repeat Kinase 2 (LRRK2) Small Molecular Inhibitors," J Med Chem 57, 921-936 (2014).
Fuji, R., et al., "Effect of selective LRRK2 kinase inhibition on nonhuman primate lung," Science Translational Medicine 7(273), 273ra15, 13 pages (2015).
Patent Cooperation Treaty, International Searching Authority, Search Report and Written Opinion for PCT/US2018/062102, 8 pages, Feb. 8, 2019.
Pub Chem, "Zppumamzimpjgp-Uhfffaoysa-N," CID 69093374, 17 pages, Create Date Nov. 30, 2012.
Taymans, J., et al., "LRRK2 Kinase Inhibition as a Therapeutic Strategy for Parkinson's Disease, Where Do We Stand?," Current Neuropharmacology 14, 214-225 (2016).

(Continued)

*Primary Examiner* — Kahsay Habte

(74) *Attorney, Agent, or Firm* — McCarter & English, LLP; Xin Zhang; Paul M. Zagar

(57) ABSTRACT

The present disclosure relates to crystalline polymorph and amorphous forms of 2-methyl-2-(3-methyl-4-(4-(methylamino)-5-(trifluoromethyl)pyrimidin-2-ylamino)-1H-pyrazol-1-yl)propanenitrile or solvates, tautomers, and pharmaceutically acceptable salts or cocrystals thereof, and processes for their preparation.

2 Claims, 9 Drawing Sheets

(56) References Cited

OTHER PUBLICATIONS

Office Action in CL 202001346 dated Sep. 16, 2021, 42 pages, with machine translation.
Examination Report issued in GCC application No. 2018-36493 dated Nov. 15, 2020, 3 pages (English translation).
Office Action in Indian Patent Application No. 202017025005 dated Nov. 30, 2021, 6 pages.
Written Opinion for Singapore Patent Application No. 11202004733W dated Nov. 11, 2021, 7 pages.
Office Action issued for Ukraine application No. a202003681 dated Jan. 18, 2022, 8 pages with English translation.
Office Action in GC Patent Application No. 2018-36493 dated Oct. 2, 2021, 4 pages.
Office Action issued for Dominican Republic application No. P2020-0117 dated Apr. 5, 2022, 7 pages with English translation.

* cited by examiner

POLYMORPHS AND SOLID FORMS OF A PYRIMIDINYLAMINO-PYRAZOLE COMPOUND, AND METHODS OF PRODUCTION

CROSS REFERENCE TO RELATED APPLICATION

This continuation application claims priority to U.S. application Ser. No. 16/447,713 filed 20 Jun. 2019, which is a continuation application of U.S. application Ser. No. 16/197,037 filed 20 Nov. 2018, now U.S. Pat. No. 10,370,361 issued on 6 Aug. 2019, and claims priority to U.S. Provisional Application No. 62/589,276 filed on 21 Nov. 2017, each of which are incorporated by reference in their entirety.

FIELD

The present disclosure relates to polymorph forms of 2-methyl-2-(3-methyl-4-((4-(methylamino)-5-(trifluoromethyl)pyrimidin-2-yl)amino)-1H-pyrazol-1-yl)propanenitrile for use in the treatment of peripheral and neurodegenerative diseases, including Parkinson's disease. The present disclosure also relates to processes to obtain polymorph forms.

BACKGROUND

Combined genetic and biochemical evidence implicates certain kinase function in the pathogenesis of neurodegenerative disorders (Christensen, K. V. (2017) Progress in medicinal chemistry 56:37-80; Fuji, R. N. et al (2015) Science Translational Medicine 7(273):273ra15; Taymans, J. M. et al (2016) Current Neuropharmacology 14(3):214-225) Kinase inhibitors are under investigation for treatment of Alzheimer's disease, Parkinson's disease, ALS and other diseases (Estrada, A. A. et al (2015) J. Med. Chem. 58(17):6733-6746; Estrada, A. A. et al (2013) J. Med. Chem. 57:921-936; Chen, H. et al (2012) J. Med. Chem. 55:5536-5545; Estrada, A. A. et al (2015) J. Med. Chem. 58:6733-6746; Chan, B. K. et al (2013) ACS Med. Chem. Lett. 4:85-90; U.S. Pat. Nos. 8,354,420; 8,569,281; 8,791,130; 8,796,296; 8,802,674; 8,809,331; 8,815,882; 9,145,402; 9,212,173; 9,212,186; and WO 2012/062783.

Multiple crystal forms with different solid state properties of a drug substance can exhibit differences in bioavailability, shelf life, physical-chemical properties including melting point, crystal morphology, intrinsic dissolution rates, solubility and stability, and behavior during processing. X-ray powder diffraction (XRPD) is a powerful tool in identifying different crystal phases by their unique diffraction patterns. Other techniques such as solid-state Nuclear Magnetic resonance NMR spectroscopy, RAMAN spectroscopy, DSC (differential scanning calorimetry) are useful as well.

The pharmaceutical industry is often confronted with the phenomenon of multiple polymorphs of the same crystalline chemical entity. Polymorphism is often characterized as the ability of a drug substance, i.e. Active Pharmaceutical Ingredient (API), to exist as two or more crystalline phases that have different arrangements and/or conformations of the molecules in the crystal lattices giving the crystals different physicochemical properties. The ability to be able to manufacture the selected polymorphic form reliably is a key factor in determining the success of the drug product.

Regulatory agencies worldwide require a reasonable effort to identify the polymorphs of the drug substance and check for polymorph interconversions. Due to the often unpredictable behavior of polymorphs and their respective differences in physicochemical properties, consistency in manufacturing between batches of the same product must be demonstrated. Proper understanding of the polymorph landscape and nature of the polymorphs of a pharmaceutical will contribute to manufacturing consistency.

Crystal structure determination at the atomic level and intermolecular interactions offer important information to establish absolute configuration (enantiomers), phase identification, quality control, and process development control and optimization. X-ray diffraction is widely recognized as a reliable tool for the crystal structure analysis of pharmaceutical solids and crystal form identification.

Availability of a single crystal of the drug substance is preferred due to the speed and accuracy of the structure determination. However, it is not always possible to obtain a crystal of suitable size for data collection. Synchrotron X-ray powder diffraction is a useful technique. In such situations the crystal structure can be solved from X-ray powder diffraction data obtained by measurements at ambient conditions and/or at variable temperature or humidity.

There is a need to develop new polymorph forms of drug substances, and methods of preparing them.

DESCRIPTION

The present disclosure relates to crystalline polymorph or amorphous forms of a pyrimidinylamino-pyrazole kinase inhibitor, referred to herein as the Formula I compound and having the structure:

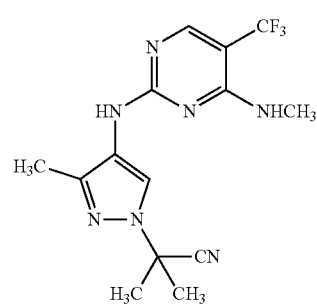

I or solvates, tautomers, or pharmaceutically acceptable salts or cocrystals thereof.

An aspect of the present disclosure is a pharmaceutical composition of a polymorph form of the Formula I compound.

Another aspect of the present disclosure is a crystalline compound, 2-methyl-2-(3-methyl-4-(4-(methylamino)-5-(trifluoromethyl)pyrimidin-2-ylamino)-1H-pyrazol-1-yl) propanenitrile, selected from:

a Form B polymorph that exhibits an X-ray powder diffraction pattern having characteristic peaks expressed in degrees 2-theta at approximately 7.0, 7.3, 16.1, 16.3, 24.1, 25.1, and 26.6;

a Form C polymorph that exhibits an X-ray powder diffraction pattern having characteristic peaks expressed in degrees 2-theta at approximately 6.4, 15.1, 21.2, 25.7, and 27.8; and a Form D polymorph that exhibits an X-ray powder diffraction pattern having characteristic peaks expressed in degrees 2-theta at approximately 9.2, 14.0, 14.8, 19.7, and 20.0.

In one aspect, provided is a Form A polymorph that exhibits an X-ray powder diffraction pattern having characteristic peaks expressed in degrees 2-theta at approximately 7.7, 9.9, 12.7, 13.6, 14.1, 15.4, 15.9, 19.2, 20.5, 21.6, 22.4 23.2, and 24.7.

In one aspect, provided is a Form B polymorph that exhibits an X-ray powder diffraction pattern having characteristic peaks expressed in degrees 2-theta at approximately 7.0, 7.3, 16.1, 16.3, 24.1, 25.1, and 26.6. In some aspects, the Form B polymorph has an X-ray powder diffraction pattern substantially free of peaks at 12.9 and 14.8±0.05 degrees 2-theta. In some aspects, the Form B polymorph is a cyclohexanol solvate. In some aspects, a differential scanning calorimetry DSC of the Form B polymorph shows two melting endotherms at about 87.9 and 103.2° C. onset.

In one aspect, provided is a Form C polymorph that exhibits an X-ray powder diffraction pattern having characteristic peaks expressed in degrees 2-theta at approximately 6.4, 8.1, 8.6, 8.8, 9.9, 10.2, 12.9, 13.8, 15.1, 15.4, 16.5, 19.8, 21.2, 22.1, 23.7, 25.7, and 27.8.

In one aspect, provided is a Form C polymorph that exhibits an X-ray powder diffraction pattern having characteristic peaks expressed in degrees 2-theta at approximately 6.4, 15.1, 21.2, 25.7, and 27.8. In aspects, the Form C polymorph further comprises a peaks at 22.1. In aspects, the Form C polymorph further comprises peaks at 16.5 and 22.1±0.05 degrees 2-theta. In some aspects, the Form C polymorph has an X-ray powder diffraction pattern substantially free of peaks at 13.6 and 14.8±0.05 degrees 2-theta. In some aspects, the Form C polymorph is an anhydrate. In some aspects, the Form C polymorph has a differential scanning calorimetry (DSC) melting endotherm at about 127.8° C. onset.

In one aspect, provided is a Form D polymorph that exhibits an X-ray powder diffraction pattern having characteristic peaks expressed in degrees 2-theta at approximately 8.0, 8.7, 9.2, 9.8, 10.4, 12.9, 13.4, 14.0, 14.8, 16.4, 18.5, 19.7, 20.0, 20.8, 23.1, 23.3, 23.9, 25.5, and 25.7.

In one aspect, provided is a Form D polymorph that exhibits an X-ray powder diffraction pattern having characteristic peaks expressed in degrees 2-theta at approximately 9.2, 14.0, 14.8, 19.7, and 20.0. In some aspects, the Form D polymorph has an X-ray powder diffraction pattern substantially free of peaks at 13.6±0.05 degrees 2-theta. In some aspects, the Form D polymorph is an anhydrate. In some aspects, the Form D polymorph has a differential scanning calorimetry (DSC) melting endotherm at about 129.1° C. onset.

In one aspect, the crystalline compounds provide herein exhibit a mass increase of less than about 1% when subjected to an increase in relative humidity from about 0% to about 95% relative humidity for about 180 minutes.

In one aspect, the crystalline compounds provide herein are stable upon exposure to about 40° C. and about 75% relative humidity for at least 6 months.

Another aspect of the present disclosure is a crystalline compound, 2-methyl-2-(3-methyl-4-(4-(methylamino)-5-(trifluoromethyl)pyrimidin-2-ylamino)-1H-pyrazol-1-yl)propanenitrile exhibiting an X-ray powder diffraction pattern having characteristic peaks expressed in ±0.3 degrees 2-theta at 6.4, 15.1, 21.2, 25.7, and 27.8.

In another aspect, the present disclosure provides a crystalline compound, 2-methyl-2-(3-methyl-4-(4-(methylamino)-5-(trifluoromethyl)pyrimidin-2-ylamino)-1H-pyrazol-1-yl)propanenitrile exhibiting an X-ray powder diffraction pattern having characteristic peaks expressed in ±0.05 degrees 2-theta at 6.4, 15.1, 21.2, 25.7, and 27.8.

An aspect of the present disclosure is a pharmaceutical composition comprising a therapeutically effective amount of a crystalline polymorph or amorphous form of the Formula I compound or solvates, tautomers, or pharmaceutically acceptable salts or cocrystals thereof, and a pharmaceutically acceptable carrier, glidant, diluent, or excipient An aspect of the present disclosure is a process for preparing a crystalline polymorph or amorphous form of the Formula I compound or solvates, tautomers, or pharmaceutically acceptable salts or cocrystals thereof.

In one aspect, provided is a process for preparing a crystalline polymorph comprising heating at 50° C. or above 2-methyl-2-(3-methyl-4-(4-(methylamino)-5-(trifluoromethyl)pyrimidin-2-ylamino)-1H-pyrazol-1-yl)propanenitrile in methyl tert-butyl ether, cyclopentyl methyl ether, ethyl acetate, isopropyl acetate, or combinations thereof and a non-polar solvent such as heptane, and then cooling the mixture whereby a Form C crystalline polymorph that exhibits an X-ray powder diffraction pattern having characteristic peaks expressed in degrees 2-theta at approximately 6.4, 15.1, 21.2, 25.7, and 27.8 degrees 2-theta is formed. In some aspects, the mixture is seeded.

In one aspect, provided is a process for preparing a crystalline polymorph comprising heating at 50° C. or above, an anhydrous solution of 2-methyl-2-(3-methyl-4-(4-(methylamino)-5-(trifluoromethyl)pyrimidin-2-ylamino)-1H-pyrazol-1-yl)propanenitrile in methyl tert-butyl ether, cyclopentyl methyl ether, ethyl acetate, isopropyl acetate, or combinations thereof, and a non-polar solvent such as heptane, and then cooling the mixture whereby a Form D crystalline polymorph that exhibits an X-ray powder diffraction pattern having characteristic peaks expressed in degrees 2-theta at approximately 9.2, 14.0, 14.8, 19.7, and 20.0 degrees 2-theta is formed. In some aspects, the mixture is seeded.

In one aspect, the crystalline polymorph provided herein is milled. In another aspect, the crystalline, anhydrate polymorph provided herein is milled.

In one aspect, provided is an amorphous compound, 2-methyl-2-(3-methyl-4-(4-(methylamino)-5-(trifluoromethyl)pyrimidin-2-ylamino)-1H-pyrazol-1-yl)propanenitrile.

In one aspect, provided is a process for preparing the amorphous compound, 2-methyl-2-(3-methyl-4-(4-(methylamino)-5-(trifluoromethyl)pyrimidin-2-ylamino)-1H-pyrazol-1-yl)propanenitrile, comprising heating a crystalline form of the compound until dissolution followed by cooling to form the amorphous compound. In one aspect the cooling is by fast cooling, such as in a dry-ice or liquid nitrogen bath.

DEFINITIONS

Figure 1:
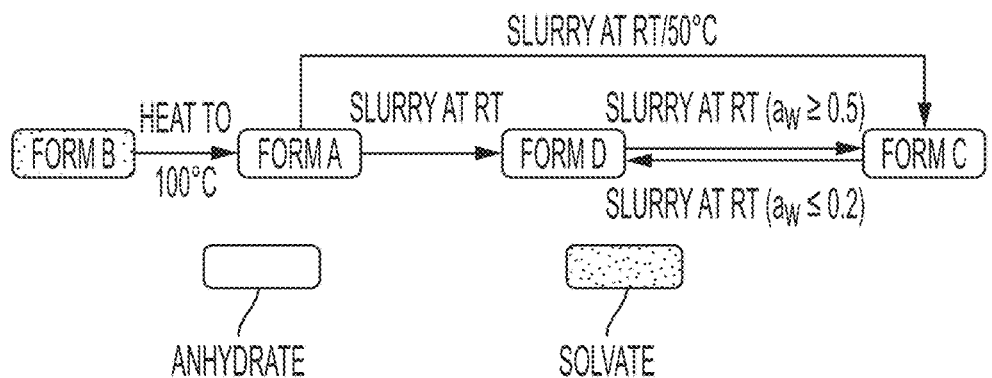
FIG. 1 shows the inter-conversion relationships between Formula I compound polymorph forms, Forms A, B, C, and D in a schematic diagram.

Unless defined otherwise, technical and scientific terms used herein have the same meaning as commonly understood by one of ordinary skill in the art to which this invention belongs, and are consistent with:

The words "comprise," "comprising," "include," "including," and "includes" when used in this specification and claims are intended to specify the presence of stated features, integers, components, or steps, but they do not preclude the presence or addition of one or more other features, integers, components, steps, or groups thereof.

As used herein, the term "about" or "approximately" when used in reference to X-ray powder diffraction pattern peak positions refers to the inherent variability of the peaks depending on, for example, the calibration of the equipment used, the process used to produce the polymorph, the age of the crystallized material and the like, depending on the instrumentation used. In this case the measure variability of the instrument was about plus/minus ±0.3 degrees 2-theta (θ). A person skilled in the art, having the benefit of this disclosure, would understand the use of "about" or "approximately" in this context unless specified otherwise (e.g. ±0.05 degrees 2-theta). The term "about" or "approximately" in reference to other defined parameters, e.g., water content, $C_{max}$, $t_{max}$, AUC, intrinsic dissolution rates, temperature, and time, indicates the inherent variability in, for example, measuring the parameter or achieving the parameter. A person skilled in the art, having the benefit of this disclosure, would understand the variability of a parameter as connoted by the use of the word about or approximately.

"Polymorph", as used herein, refers to the occurrence of different crystalline forms of a compound differing in packing or conformation/configuration but with the same chemical composition. Crystalline forms have different arrangements and/or conformations of the molecule in the crystal lattice. Solvates are crystal forms containing either stoichiometric or nonstoichiometric amounts of a solvent. If the incorporated solvent is water, the solvate is commonly known as a hydrate. Hydrates/solvates may exist as polymorphs for compounds with the same solvent content but different lattice packing or conformation. Therefore, a single compound may give rise to a variety of polymorphic forms where each form has different and distinct physical properties, such as solubility profiles, melting point temperatures, hygroscopicity, particle shape, morphology, density, flowability, compactibility and/or X-ray diffraction peaks. The solubility of each polymorph may vary, thus, identifying the existence of pharmaceutical polymorphs is essential for providing pharmaceuticals with predictable solubility profiles. It is desirable to characterize and investigate all solid state forms of a drug, including all polymorphic forms, and to determine the stability, dissolution and flow properties of each polymorphic form. Polymorphic forms of a compound can be distinguished in a laboratory by X-ray diffractometry and by other methods such as, infrared or Raman or solid-state NMR spectrometry. For a general review of polymorphs and the pharmaceutical applications of polymorphs see G. M. Wall, Pharm Manuf. 3:33 (1986); J. K. Haleblian and W. McCrone, J. Pharm. Sci., 58:911 (1969); "Polymorphism in Pharmaceutical Solids, Second Edition (Drugs and the Pharmaceutical Sciences)", Harry G. Brittain, Ed. (2011) CRC Press (2009); and J. K. Haleblian, J. Pharm. Sci., 64, 1269 (1975), all of which are incorporated herein by reference.

The acronym "XRPD" means X-ray powder diffraction, an analytical technique which measures the diffraction of X-rays in the presence of a solid component with a display of the X-ray diffraction pattern. The X-ray diffraction pattern may be made using CuKα1 radiation. Materials which are crystalline and have regular repeating arrays of atoms generate a distinctive powder pattern. Materials with similar unit cells will give X-ray diffraction patterns that are similar in position as measured in °2θ (theta). Solvates which exhibit this property are called isostructural or isomorphous solvates. The intensity of the reflections varies according to the electron density causing diffraction as well as sample, sample preparation, and instrument parameters. Analysis of XRPD data is based upon the general appearance of the measured powder pattern(s) with respect to the known response of the X-ray diffraction system used to collect the data. For diffraction peaks that may be present in the powder pattern, their positions, shapes, widths, and relative intensity distributions can be used to characterize the type of solid state order in the powder sample. The position, shape, and intensity of any broad diffuse scatter (halos) on top of the instrumental background can be used to characterize the level and type of solid state disorder. The combined interpretation of the solid state order and disorder present in a powder sample provides a qualitative measure of the macrostructure of the sample.

The term "cocrystal" refers to a crystalline molecular complex composed of two or more different molecular compounds generally in a stoichiometric ratio which are neither solvates nor simple salts. The cocrystal consists of a hydrogen-bonded complex with a "pharmaceutically acceptable" coformer (Aitipamula, S. et al (2012) Cryst. Growth Des. 12(5):2147-2152). Coformers include, but are not limited to, acetylsalicylic acid, trans-acontic acid, adipic acid, L-ascorbic acid, benzoic acid, citric acid, fructose, fumaric acid, gallic acid, glucose, glutaric acid, hippuric acid, 4-hydroxybenzoic acid, maleic acid, malonic acid, mannitol, nicotinamide, nicotinic acid, phenylalanine, riboflavin, salicylic acid, succinic acid, and vanillic acid.

The phrase "pharmaceutically acceptable salt" as used herein, refers to pharmaceutically acceptable organic or inorganic salts of a compound of the invention. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate", ethanesulfonate, benzenesulfonate, p-toluenesulfonate, and pamoate (i.e., 1,1'-methylene-bis-(2-hydroxy-3-naphthoate)) salts. Other salts include acid salts such as coformers described above. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure.

Instances where multiple charged atoms are part of the pharmaceutically acceptable salt can have multiple counter ions. Hence, a pharmaceutically acceptable salt can have one or more charged atoms and/or one or more counter ion.

The desired pharmaceutically acceptable salt may be prepared by any suitable method available in the art. For example, treatment of the free base with an inorganic acid, such as hydrochloric acid, hydrobromic acid, sulfuric acid, nitric acid, phosphoric acid, and the like, or with an organic acid, such as acetic acid, maleic acid, succinic acid, mandelic acid, methanesulfonic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like. Acids which are generally considered suitable for the formation of pharmaceutically useful or acceptable salts from basic pharmaceutical compounds are discussed, for example, by Stahl P H, Wermuth C G, editors. Handbook of Pharmaceutical Salts; Properties, Selection and Use, $2^{nd}$ Revision (International Union of Pure and Applied Chemistry). 2012, New York: Wiley-VCH; S. Berge et al, Journal of Pharmaceutical Sciences (1977) 66(1) 1 19; P. Gould, International J. of Pharmaceutics (1986) 33 201 217; Anderson et al, The Practice of Medicinal Chemistry (1996), Academic Press, New York; Remington's Pharmaceutical Sciences, $18^{th}$ ed., (1995) Mack Publishing Co., Easton Pa.; and in The Orange Book (Food & Drug Administration, Washington, D.C. on their website). These disclosures are incorporated herein by reference thereto.

The phrase "pharmaceutically acceptable" indicates that the substance or composition must be compatible chemically and/or toxicologically, with the other ingredients comprising a formulation, and/or the mammal being treated therewith.

A "solvate" refers to an association or complex of one or more solvent molecules and a compound of the invention. Examples of solvents that form solvates include, but are not limited to, water, isopropanol, ethanol, methanol, cyclohexanol, DMSO, ethyl acetate, acetic acid, and ethanolamine. Other solvents that may form solvates include the Class 2 and 3 groups from "Q3C—Tables and List Guidance for Industry:" (June 2017) US Dept. HHS, Food and Drug Administration, Center for Drug Evaluation and Research (CDER) and Center for Biologics Evaluation and Research (CBER). The Class 2 group of solvents that may form solvates are: Acetonitrile, Chlorobenzene, Chloroform, Cyclohexane, Cumene, 1,2-Dichloroethene, Dichloromethane, 1,2-Dimethoxyethane, N,N-Dimethylacetamide, N,N-Dimethylformamide, 1,4-Dioxane, 2-Ethoxyethanol, Ethyleneglycol, Formamide, Hexane, Methanol, 2-Methoxyethanol, Methylbutyl ketone, Methylcyclohexane, Methylisobutylketone, N-Methylpyrrolidone, Nitromethane, Pyridine, Sulfolane, Tetrahydrofuran (THF), Tetralin, Toluene, Trichloroethene, and Xylene. The Class 3 group of solvents that may also form solvates are: Acetic acid, Heptane, Acetone, Isobutyl acetate, Anisole, Isopropyl acetate, 1-Butanol, Methyl acetate, 2-Butanol, 3-Methyl-1-butanol, Butyl acetate, Methylethyl ketone, tert-Butylmethyl ether, 2-Methyl-1-propanol, Dimethyl sulfoxide, Pentane, Ethanol, 1-Pentanol, Ethyl acetate, 1-Propanol, Ethyl ether, 2-Propanol, Ethyl formate, Propyl acetate, Formic acid, and Triethylamine.

The term "hydrate" refers to the complex where the solvent molecule is water.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., "Stereochemistry of Organic Compounds", John Wiley & Sons, Inc., New York, 1994. The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

Formula I Compound

The present disclosure includes polymorphs and amorphous forms of Formula I compound, (CAS Registry Number 1374828-69-9), having the structure:

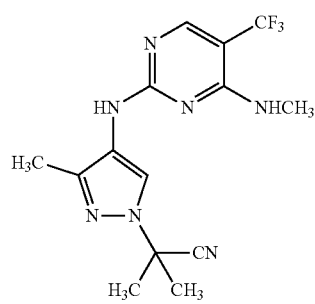

I and named as: 2-methyl-2-(3-methyl-4-(4-(methylamino)-5-(trifluoromethyl)pyrimidin-2-ylamino)-1H-pyrazol-1-yl)propanenitrile (WO 2012/062783; U.S. Pat. No. 8,815,882; US 2012/0157427, each of which are incorporated by reference). As used herein, the Formula I compound includes tautomers, and pharmaceutically acceptable salts or cocrystals thereof. The Formula I compound is the API (Active Pharmaceutical Ingredient) in formulations for use in the treatment of neurodegenerative and other disorders, with pKa when protonated calculated at 6.7 and 2.1.

Crystallization and Screening of Formula I Compound

Initial polymorph screening experiments were performed using a variety of crystallization or solid transition methods, including: anti-solvent addition, reverse anti-solvent addition, slow evaporation, slow cooling, slurry at room temperature (RT), slurry at 50° C., solid vapor diffusion, liquid vapor diffusion, and polymer induced crystallization. By all these methods, the Form A crystal type was identified. Polarized light microscopy (PLM) images of Form A obtained from various polymorph screening methods were collected (Example 5). Particles obtained via anti-solvent addition showed small size of about 20 to 50 microns (μm) diameter while slow evaporation, slow cooling (except for THF/isooctane), liquid vapor diffusion and polymer-induced crystallization resulted in particles with larger size. Adding isooctane into a dichloromethane (DCM) solution of the Formula I compound produced particles with the most uniform size. Crude Formula I compound crystallized from THF/n-heptane and then was micronized. A crystallization procedure was developed to control particle size.

A total of four crystal forms (Forms A, B, C, and D) and an amorphous form E of Formula I compound were prepared, including 3 anhydrates (Form A, C, and D) and one solvate (Form B). Slurry competition experiments indicated that Form D was thermodynamically more stable when the water activity $a_w \leq 0.2$ at RT, while Form C was more stable when $a_w \geq 0.5$ at RT. The 24 hrs solubility evaluation showed the solubility of Form A, C and D in $H_2O$ at RT was 0.18, 0.14 and 0.11 mg/mL, respectively. DVS (dynamic vapor sorption) results indicated that Form A and D were non-hygroscopic as defined by less than 0.1% reversible water intake in DVS, while Form C was slightly hygroscopic. Certain characterization data and observations of the crystal forms are shown in Table 1.

date, a total of four crystal forms A, B, C, and D have been prepared. An amorphous form E has also been prepared. All of the crystal forms were characterized by X-ray powder diffraction (XRPD) by the procedures of Example 6, and thermo gravimetric analysis (TGA) and differential scanning calorimetry (DSC) by the procedures of Example 7. Form identification study confirmed that Form A, C and D were anhydrates and Form B was a cyclohexanol solvate. Characterization summary for all the crystal forms was presented in Table 1. The thermodynamic stability relationship between three anhydrates (Form A, C and D) was investigated via slurry competition experiments. Detailed inter-conversion relationship was depicted in the schematic diagram (shown in FIG. 1). The inter-conversion relationship between Form C and D was associated with the solvent effect of $H_2O$. Form D was thermodynamically more stable when $a_w \leq 0.2$ at room temperature (RT, 25±2° C.), while Form C was more stable when $a_w \geq 0.5$ at RT. Forms A, C and D were further evaluated by 24 hrs solubility in $H_2O$ and hygroscopicity. The 24 hrs solubility of Form A, C and D in $H_2O$ at RT was measured to be 0.18, 0.14 and 0.11 mg/mL, respectively. No form change was observed after 24 hrs solubility evaluation. Dynamic vapor sorption (DVS) data showed that Form A and D were non-hygroscopic, while Form C was slightly hygroscopic. Based on the characterization and evaluation results, both of Form C and D showed superior physicochemical properties, including high crystallinity, low TGA weight (Wt) loss and single sharp DSC endotherm. However, considering the solvent effect of $H_2O$ associated with the inter-conversion relationship between Form C and D, it may be beneficial to control the water content in process solvents and the relative humidity of environment during the manufacturing and storage ($a_w \geq 0.5$ for Form C, $a_w \leq 0.2$ for Form D).

Figure 2:
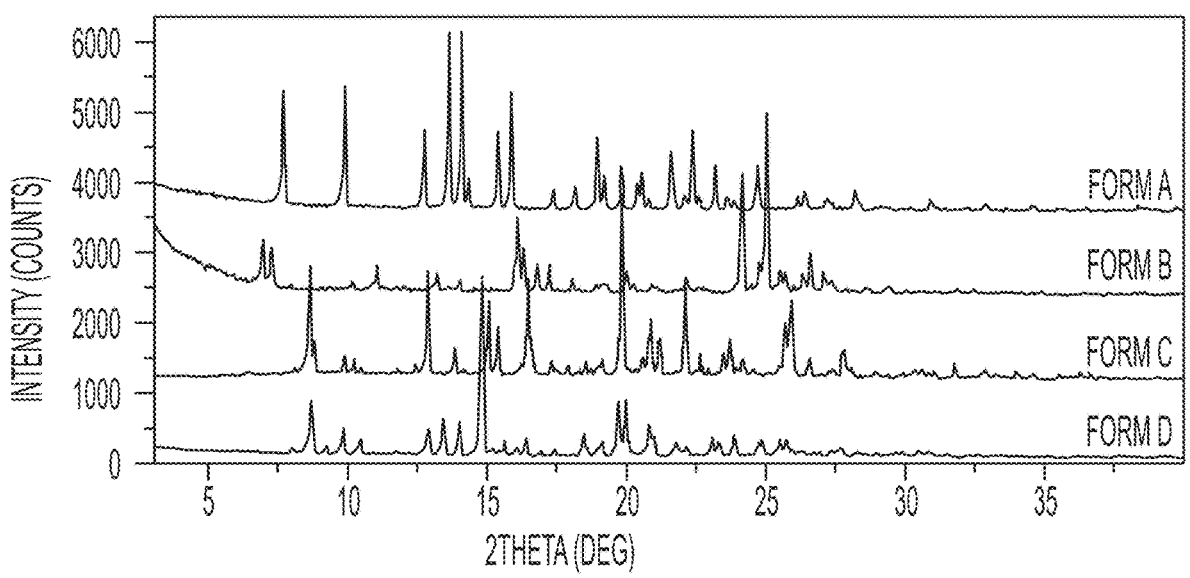
FIG. 2 shows an overlay of the XRPD patterns of Formula I compound polymorph forms, Forms A, B, C, and D.

A total of four crystal forms A, B, C, and D of Formula I compound and an amorphous form E were prepared. An overlay of XRPD patterns of Formula I compound crystal forms are displayed in FIG. 2.

Inter-Conversion of Crystal Forms

Slurry competition experiments were performed to investigate the inter-conversion relationship between three anhydrates (Form A, C, and D). Since Formula I compound showed low solubility (<2 mg/mL) in $H_2O$ and non-polar

TABLE 1

Characterization summary for crystal forms of Formula I compound

| Crystal Form | Wt Loss in TGA (%) | Endotherm in DSC (° C., onset) | Form Identity | 24 Hrs Solubility RT in $H_2O$ at (mg/mL) | Hygroscopicity | Enthalpy ΔH (J/g) |
|---|---|---|---|---|---|---|
| Form A | 0.6 | 122.8 | Anhydrate | 0.18 | Nonhygroscopic | 91.2 |
| Form B | 13.9 | 87.9, 103.2 | Cyclohexanol solvate | NA | NA | 65.3 |
| Form C | 0.8 | 127.8 | Anhydrate | 0.14 | Slightly hygroscopic | 94.37 |
| Form D | 0.5 | 129.1 | Anhydrate | 0.11 | Nonhygroscopic | 90.28 |

Differential Scanning calorimetry (DSC) analysis of Forms A and C showed that Form C had higher melting point and higher heat of fusion (Table 1), suggesting that the two forms are monotropic with Form C being the more stable form. Competitive slurry experiments with 1:1 Form A and C in a variety of solvents always produced Form C confirming that Form C was more stable than Form A. In accordance with this, Form C was produced even when the crystallization batch was seeded with seeds of Form A.

Polymorphs of Formula I Compound

The physical characterization, and inter-conversion relationships were evaluated to identify a suitable crystal form of the Formula I compound for further development. To solvents (e.g., n-heptane, cyclohexane) and good solubility (>40 mg/mL) in other solvents, mixed solvent systems were used for most of the slurry competition experiments. Slurry competition was first performed between Form A and C at RT and 50° C. Form C was obtained after slurrying for 40 hrs at RT or 2 hrs at 50° C. Further slurrying for an additional three weeks resulted in Form D as a new anhydrate, except when exposed to $H_2O$. Therefore, slurry competition was further performed between Form C and D in various solvent systems. The solvent effect of $H_2O$ was discovered to be associated with the inter-conversion relationship between Form C and D, with form D forming under anhydrous conditions.

To understand the thermodynamic stability relationship between Form A and Form C, slurry competition experiments were performed at RT and 50° C. in different solvent systems, including acetone/n-heptane, methyl tert-butylether (MTBE)/heptane, and water. Form A was used to saturate the corresponding solvent before filtered to obtain a near-saturated solution. Equal amount of Form A and C samples were weighed and then mixed with the prepared near-saturated solution to form a new suspension, which was stirred magnetically (1000 rpm) at RT and 50° C. The XRPD patterns of remaining solids after slurry were measured. Form C was obtained after slurry at RT for 40 hrs or slurry at 50° C. for 2 hrs, indicating Form C is thermodynamically more stable than Form A from RT to 50° C. Further slurrying for over 3 weeks resulted in the formation of Form D, except for in $H_2O$ at 50° C. Form D was obtained via slurrying Form A in MTBE/n-heptane (1:4, v/v) at RT for 1 day, with the addition of Form D sample as seeds.

To further understand the thermodynamic stability relationship between Form C and Form D, slurry competition experiments were performed at RT and 70° C. in various solvent systems, including methyl tert-butylether/heptane, water, cyclohexane, and ethanol/isooctane. Equal amount of Form C and D samples were weighed and then mixed with the near-saturated solution of Form A in corresponding solvent to form a suspension, which was stirred magnetically (~1000 rpm) at different temperatures. The XRPD patterns of remaining solids after slurry were measured. Form C was obtained after slurry in $H_2O$ at RT/70° C. and in EtOH/isooctane (1:19) at RT, while Form D was obtained in the other solvent systems. Based on these results, the inter-conversion relationship between Form C and D is postulated to be associated with the solvent effect of $H_2O$ or EtOH. To investigate the influence of $H_2O$ in process solvents on the inter-conversion relationship between Form C and D, slurry competition of Form C and Form D was performed in EtOAc/n-heptane (1:4, v/v) with and without $H_2O$ saturation. Form C was obtained in EtOAc/n-heptane (1:4, v/v) saturated with $H_2O$, while Form D was obtained in the solvent system without pre-treatment. Water content in process solvents were monitored and controlled during the manufacturing of Form C or D samples. Slurry competition of Form C and Form D was performed in acetone/$H_2O$ system with different water activities (aw~0.2, 0.5, 0.8) at RT. Form D was obtained when aw~0.2 at RT, while Form C was obtained when aw~0.5, 0.8 at RT. Water activity (or relative humidity) was monitored and controlled during the manufacture and storage of Form C or D samples.

The solubility at 24 hrs of Forms A, C, and D was measured in water at RT. Form A, Form C, and Form D samples were suspended into $H_2O$ with dose concentration of 10 mg/mL. After slurrying the suspensions at RT for 24 hrs (1000 rpm), the supernatants were separated for HPLC solubility measurement and the residual solids were characterized by XRPD. The solubility of Form A, C, and D in $H_2O$ were measured to be 0.18, 0.14 and 0.11 mg/mL, respectively. No form change was observed for Forms A, C, or D after 24 hrs solubility evaluation at RT.

Single Crystal Structure Determination

The crystal structures of Forms A, C, and D were determined by Single-crystal X-ray diffraction (SCXRD) by the procedures of Example 4. The single crystal of Form A of adequate quality for the SCXRD was obtained via liquid vapor diffusion from n-butyl acetate/cyclohexane solvent system (n-butyl acetate was the solvent while cyclohexane was the anti-solvent) at RT. The crystallographic data and the information on structure refinements are listed in Example 4. The SCXRD characterization revealed that the crystal adopted the $P2_1/n$ space group with a=5.325(2) Å, b=13.005(5) Å, c=24.778(9) Å; α=90°, β=94.408(11)°, γ=90°.

Figure 3:
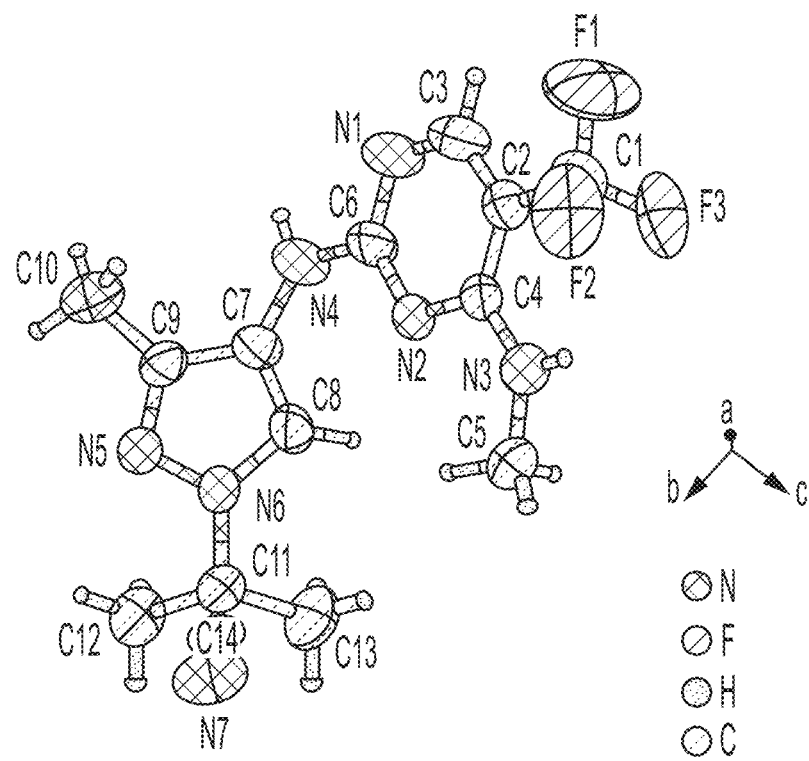
FIG. 3 shows the single crystal X-ray structure of Form A polymorph.

The asymmetric unit of the single crystal of the Form A polymorph is displayed in FIG. 3. The asymmetric unit is comprised of only one Formula I molecule, indicating the Form A is an anhydrate.

Figure 6:
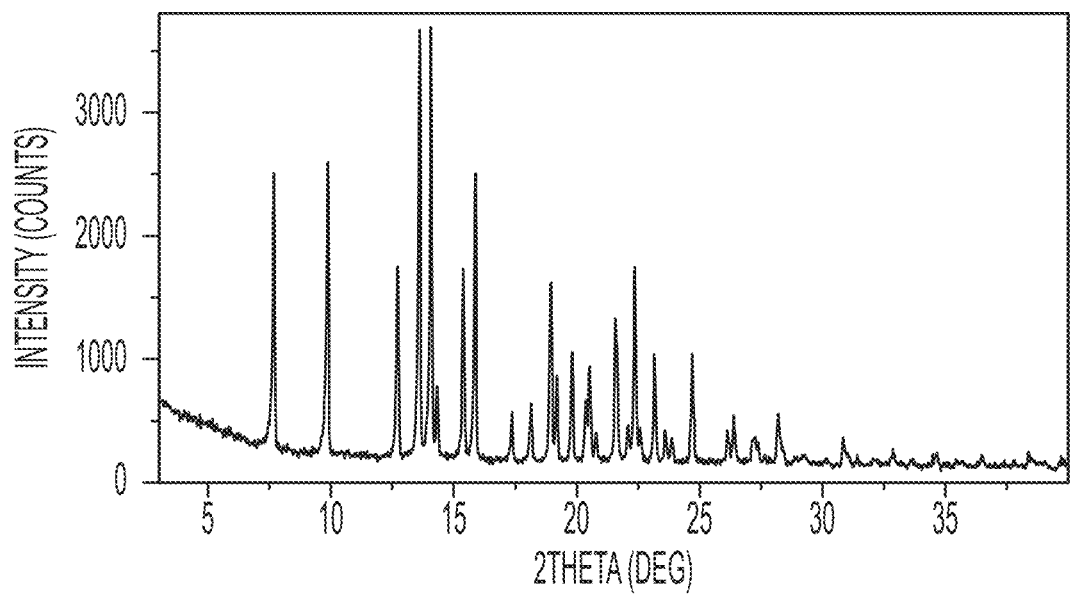
FIG. 6 shows the XRPD pattern of Form A (anhydrate) polymorph.

The hydrogen bonds in Form A single crystal structure show three dimensional (3-D) packing of Formula I molecules sustained by intermolecular H-bonds (N3-H3 . . . N7, N-4 . . . N1) as well as additional Van der Waals interactions. The calculated XRPD pattern is consistent with the experimental XRPD pattern of Form A (FIG. 6).

Figure 4:
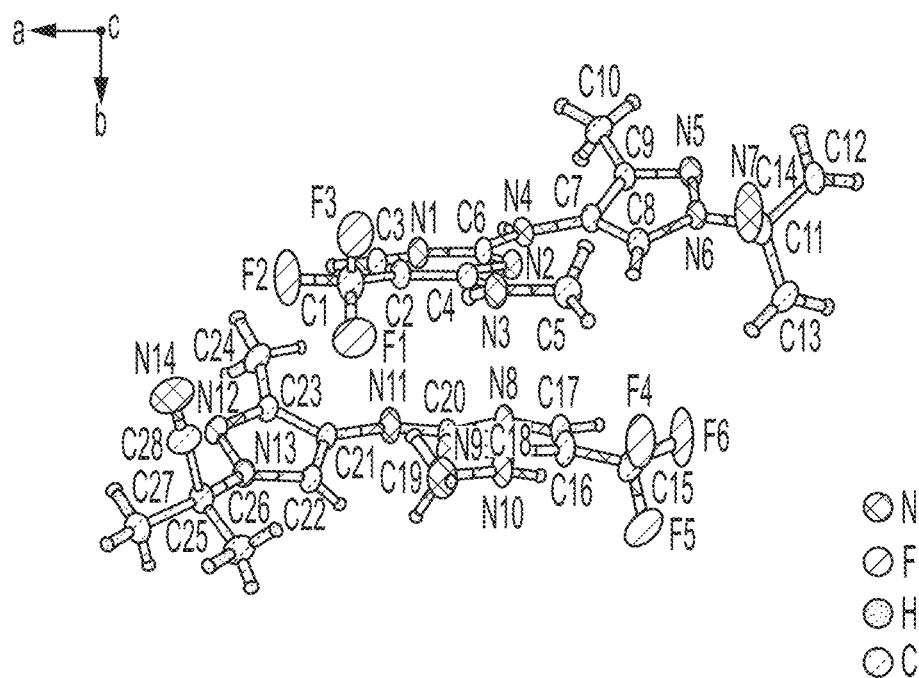
FIG. 4 shows the single crystal X-ray structure of Form C polymorph.
Figure 5:
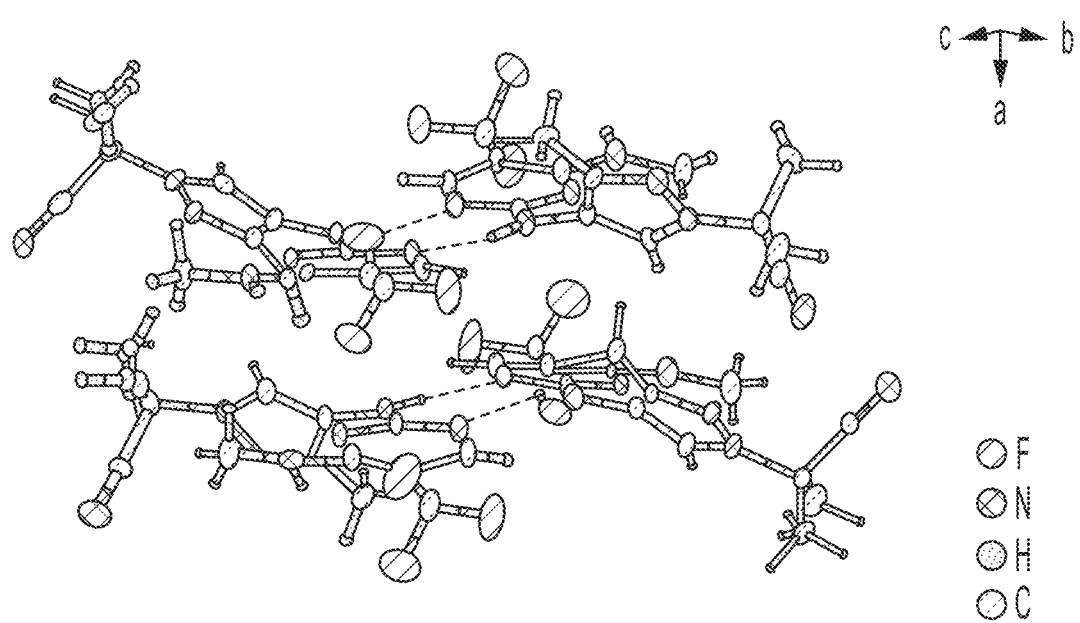
FIG. 5 shows the single crystal X-ray structure of Form D polymorph.

Single crystal X-ray structures of Form C (FIG. 4) and Form D (FIG. 5) show the unit crystal interactions of these forms, and density (Table 2).

TABLE 2

Crystal density of Forms A, C, D

| Crystal Form | Density (calculated from SCXRD, g/cm$^3$) |
|---|---|
| Form A | 1.318 |
| Form C | 1.367 |
| Form D | 1.390 |

Dynamic Vapor Sorption DVS

To investigate the solid form stability as a function of humidity, Dynamic Vapor Sorption (DVS) isotherm plots of Form A, Form C, and Form D were collected at 25° C. between 0 and 95% relative humidity (RH) by the procedures of Example 8. Based on the DVS results, Form A (0.04% water uptake at 80% RH at 25° C.) and Form D (0.05% water uptake at 80% RH at 25° C.) were non-hygroscopic, while Form C (0.6% water uptake at 80% RH at 25° C.) was slightly hygroscopic. No form change was observed after DVS evaluation.

X-Ray Powder Diffraction Analysis

Analysis of X-ray Powder Diffraction (XRPD) patterns was conducted with commercially available, analytical software by the procedures of Example 6. XRPD is useful for fingerprinting of different crystalline phases, polymorphs, hydrates or solvates by their unique diffraction patterns. Along the abscissa (horizontal axis) is plotted the 2-theta (Θ) values—the series of angles between the incident and diffracted beams. The ordinate (vertical axis) records the intensity of the scattered X-ray registered by detector. The set of peaks act as a unique fingerprint of the crystallographic unit cell within a crystalline substance. The crystallographic unit cell is the smallest atomic-scale 3D fragment that is repeated periodically in three dimensions throughout the entire crystal. All crystalline substances are distinguished by their crystallographic unit cells (and therefore peak positions). By comparing measured peak positions with those held in a database, the crystalline substance may be identified uniquely. For pure substances, the positions of all peaks are generally a function of three parameters: a, b, c and three angles: alpha, beta, gamma (α, β, γ) defining the elementary parallelepiped that constitutes the crystallographic unit cell.

Formula I Compound Solid Forms

Figure 7:
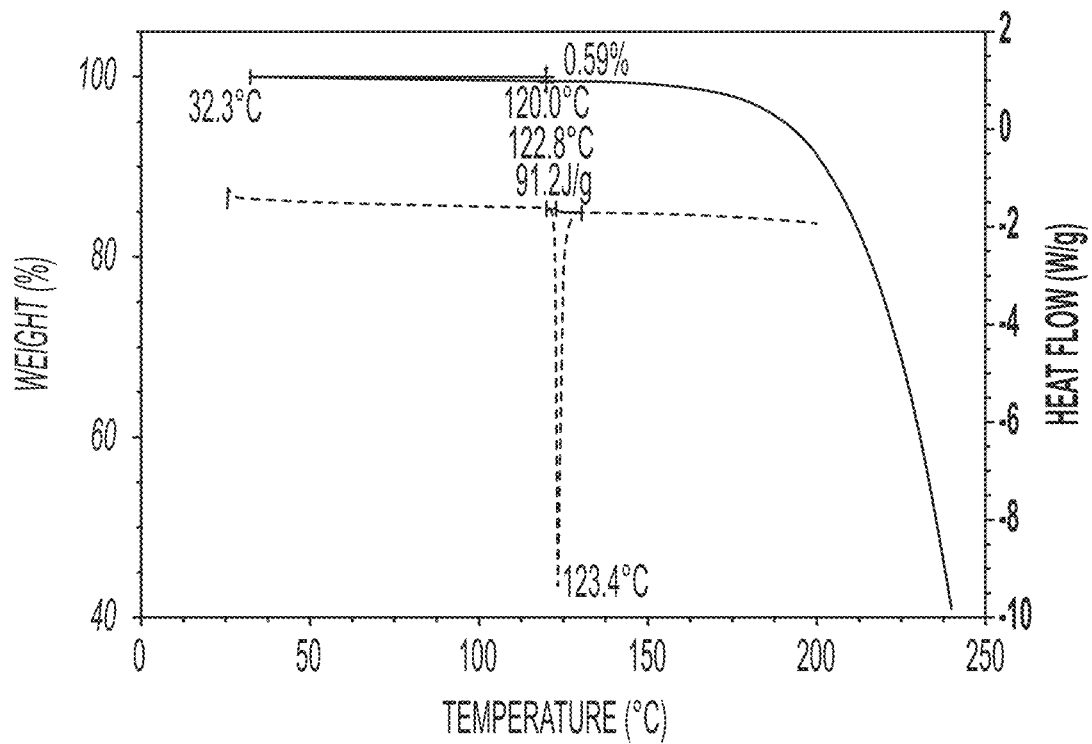
FIG. 7 shows the TGA and DSC data of Form A (anhydrate) polymorph.

Form A was characterized by XRPD, TGA and DSC. The XRPD pattern is shown in FIG. 6 and shows Form A is crystalline. The XRPD Peak Search Report for Formula I, Form A is compiled in Table 3. TGA and DSC data are shown in FIG. 7. A weight loss of 0.6% was observed up to 120° C. on the TGA curve. The DSC result exhibited a sharp endotherm at 122.8° C. (onset temperature). Based on the low TGA weight loss and the only sharp DSC endotherm, Form A is postulated to be an anhydrate.

TABLE 3

XRPD Peak Search Report for Formula I, Form A

| Pos. [°2Th.] | Height [cts] | d-spacing [Å] | Rel. Int. [%] |
|---|---|---|---|
| 7.7 | 2149 | 11.5 | 61.1 |
| 9.9 | 2255 | 9.0 | 64.1 |
| 12.7 | 1545 | 7.0 | 43.9 |
| 13.6 | 3517 | 6.5 | 100.0 |
| 14.1 | 3373 | 6.3 | 95.9 |
| 15.4 | 1442 | 5.8 | 41.0 |
| 15.9 | 2332 | 5.6 | 66.3 |
| 19.2 | 658 | 4.6 | 18.7 |
| 20.5 | 726 | 4.3 | 20.6 |
| 21.6 | 1076 | 4.1 | 30.6 |
| 22.4 | 1515 | 4.0 | 43.1 |
| 23.2 | 855 | 3.8 | 24.3 |
| 24.7 | 808 | 3.6 | 23.0 |

Figure 8:
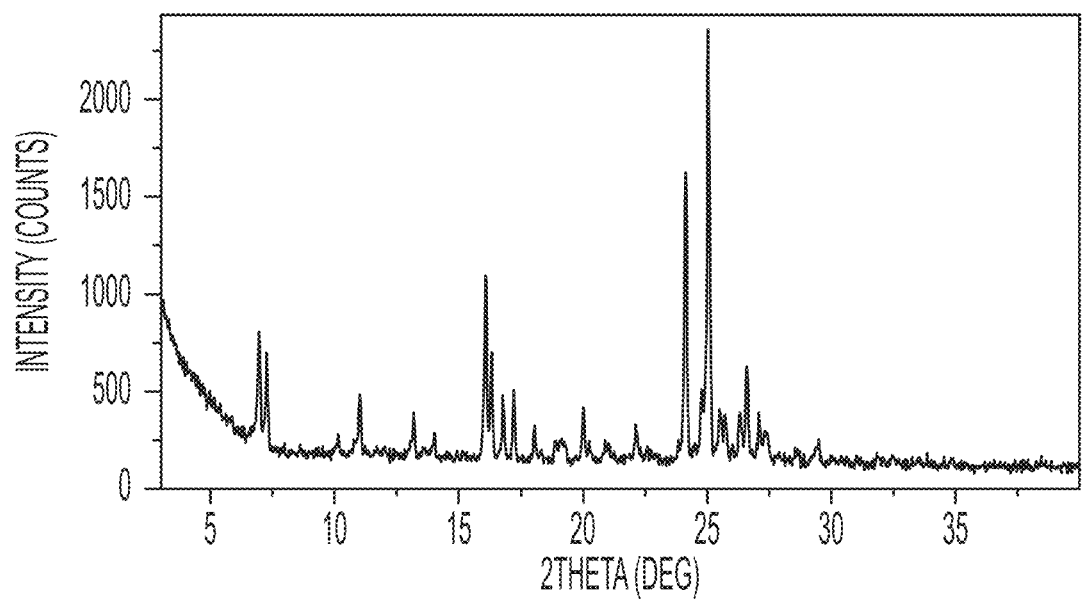
FIG. 8 shows the XRPD pattern of Form B (cyclohexanol solvate) polymorph.
Figure 9:
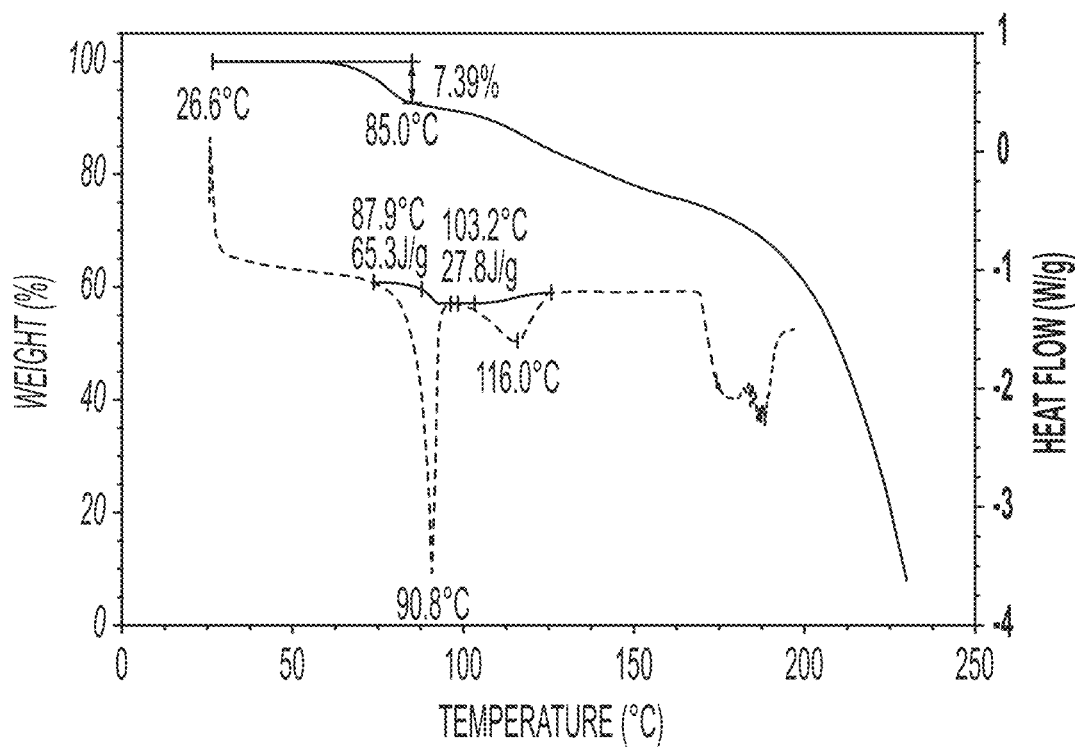
FIG. 9 shows the TGA and DSC data of Form B (cyclohexanol solvate) polymorph.

Form B was characterized by XRPD, TGA and DSC, and obtained via slurrying Form A in isobutyl acetate/cyclohexanol (1:9, v/v) at RT for 1 week. The XRPD pattern is shown in FIG. 8. The XRPD Peak Search Report for Formula I, Form B is compiled in Table 4. TGA and DSC data are displayed in FIG. 9. A weight loss of 13.9% up to 120° C. on the TGA curve and two endotherms at 87.9° C. and 103.2° C. (onset temperature) on the DSC curve were observed. The NMR spectrum (1H) indicated the molar ratio of cyclohexanol/API was 0.5:1 (12.9 wt %). Combined with the heating and 1H NMR results, Form B is postulated to be a cyclohexanol solvate.

TABLE 4

XRPD Peak Search Report for Formula I, Form B

| Pos. [°2Th.] | Height [cts] | d-spacing [Å] | Rel. Int. [%] |
|---|---|---|---|
| 7.0 | 532 | 12.7 | 25.8 |
| 7.3 | 444 | 12.2 | 21.5 |
| 16.1 | 948 | 5.5 | 46.0 |
| 16.3 | 551 | 5.4 | 26.7 |
| 24.1 | 1469 | 3.7 | 71.2 |
| 25.1 | 2063 | 3.6 | 100.0 |
| 26.6 | 489 | 3.4 | 23.7 |

Figure 10:
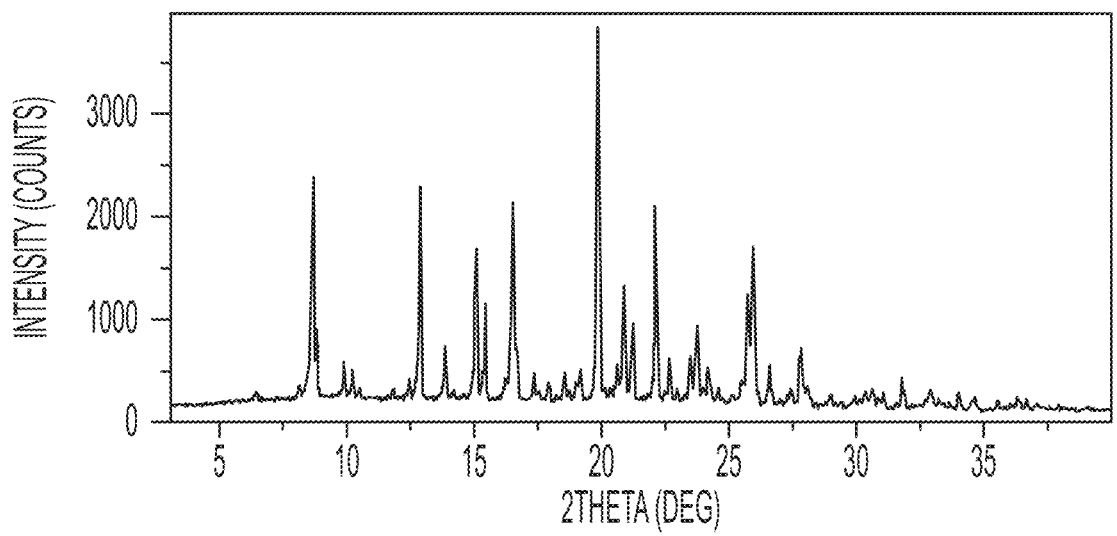
FIG. 10 shows the XRPD pattern of Form C (anhydrate) polymorph.
Figure 11:
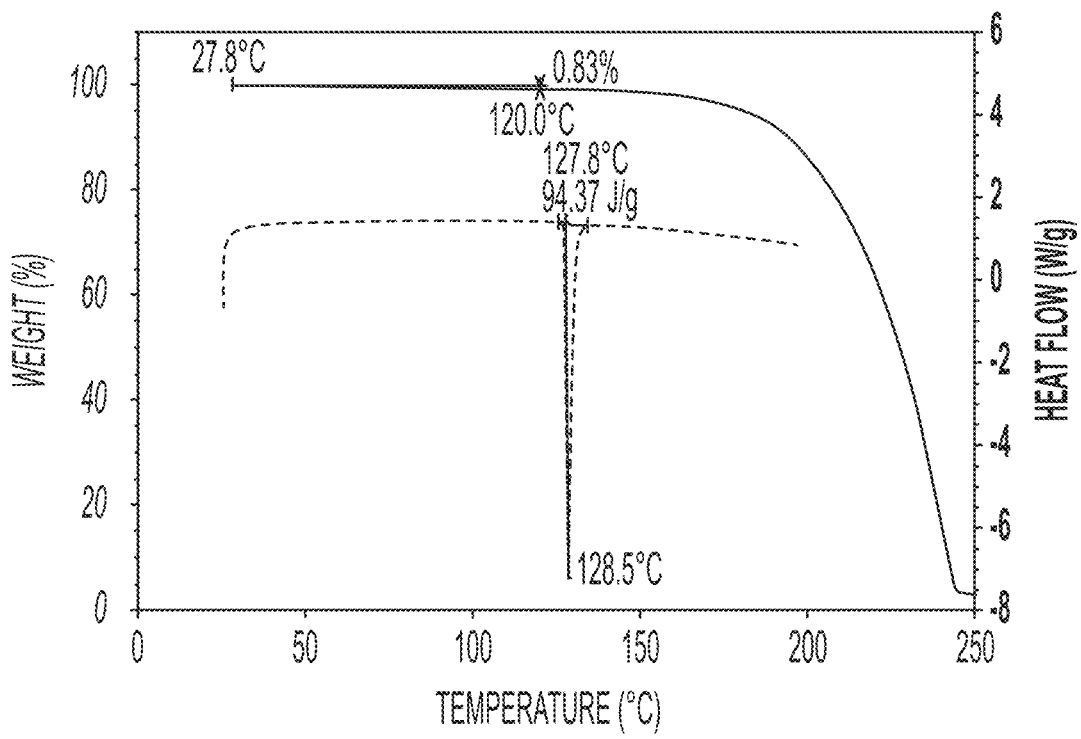
FIG. 11 shows the TGA and DSC data of Form C (anhydrate) polymorph.

Form C was characterized by XRPD, TGA and DSC. The XRPD pattern is shown in FIG. 10. The XRPD Peak Search Report for Formula I, Form C is compiled in Table 5. TGA and DSC data are displayed in FIG. 11. A weight loss of 0.8% up to 120° C. on the TGA curve and a sharp endotherm at 127.8° C. (onset temperature) on the DSC curve were observed. Based on the low TGA weight loss and the only sharp DSC endotherm, Form C is postulated to be an anhydrate.

TABLE 5

XRPD Peak Search Report for Formula I, Form C

| Pos. [°2Th.] | Height [cts] | d-spacing [Å] | Rel. Int. [%] |
|---|---|---|---|
| 6.4 | 107 | 13.8 | 2.9 |
| 8.1 | 173 | 10.9 | 4.7 |
| 8.6 | 2175 | 10.2 | 59.2 |
| 8.8 | 738 | 10.1 | 20.1 |
| 9.9 | 401 | 9.0 | 10.9 |
| 10.2 | 333 | 8.7 | 9.1 |
| 12.9 | 2135 | 6.9 | 58.1 |
| 13.8 | 581 | 6.4 | 15.8 |
| 15.1 | 1496 | 5.9 | 40.7 |
| 16.5 | 1952 | 5.4 | 53.1 |
| 19.8 | 3675 | 4.5 | 100.0 |
| 21.2 | 793 | 4.2 | 21.6 |
| 22.1 | 1958 | 4.0 | 53.3 |

TABLE 5-continued

XRPD Peak Search Report for Formula I, Form C

| Pos. [°2Th.] | Height [cts] | d-spacing [Å] | Rel. Int. [%] |
|---|---|---|---|
| 23.7 | 790 | 3.6 | 21.5 |
| 25.7 | 1065 | 3.5 | 29.0 |
| 27.8 | 570 | 3.2 | 15.5 |

Figure 12:
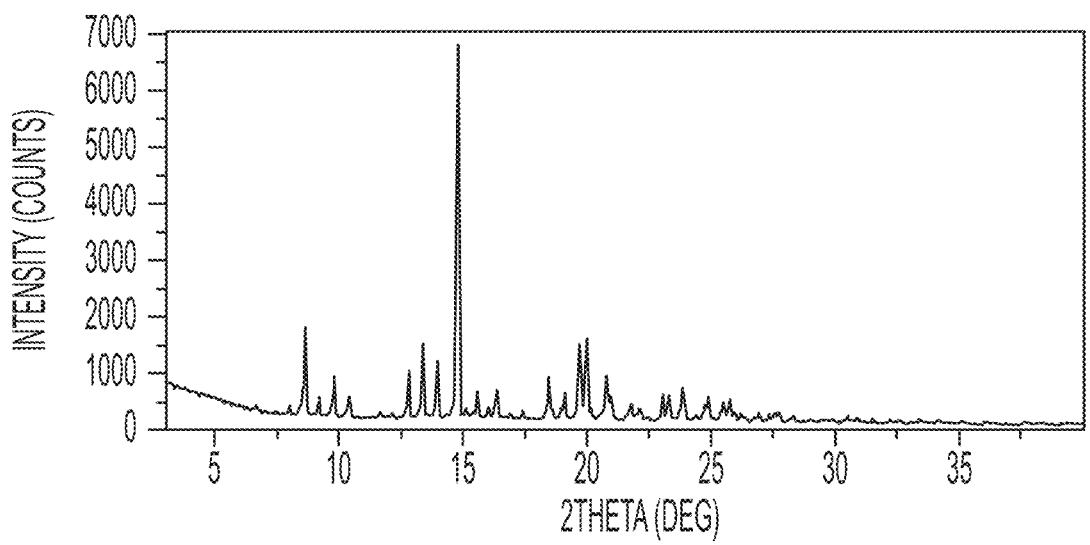
FIG. 12 shows the XRPD pattern of Form D (anhydrate) polymorph.
Figure 13:
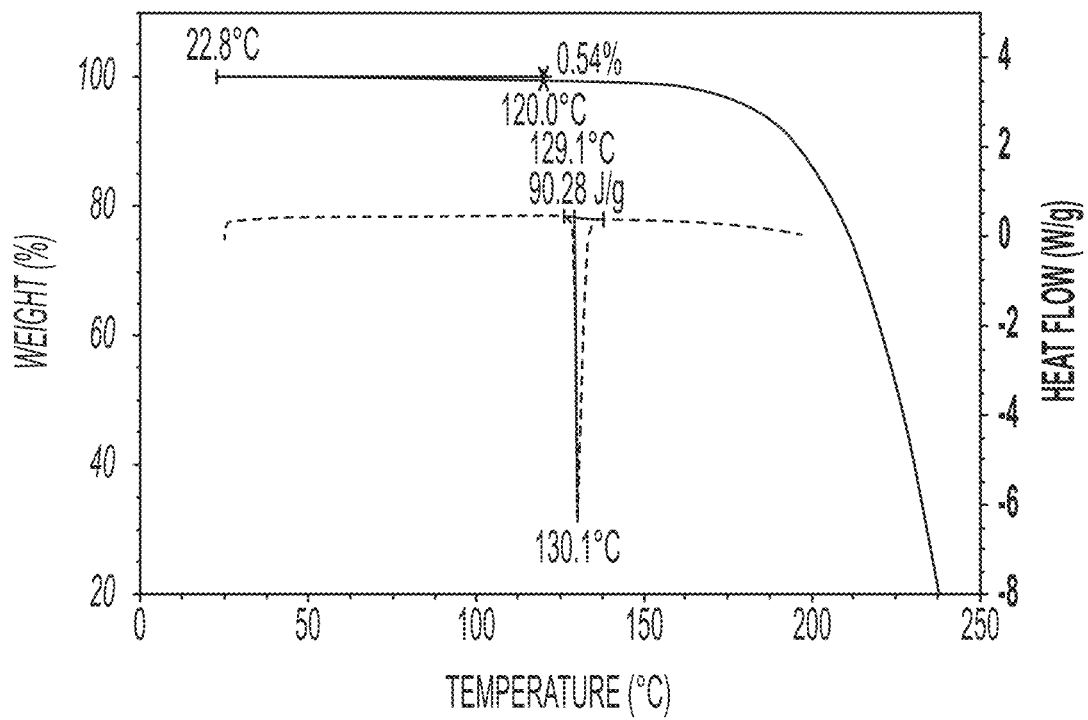
FIG. 13 shows the TGA and DSC data of Form D (anhydrate) polymorph.

Form D seeds were obtained via slurrying Form A in MTBE/n-heptane (1:4, v/v) at RT for 1 day, with the addition of Form D sample obtained from slurry competition. The XRPD pattern is shown in FIG. 12. The XRPD Peak Search Report for Formula I, Form D is compiled in Table 6. TGA and DSC data are displayed in FIG. 13. A weight loss of 0.2% up to 120° C. on the TGA curve and a sharp endotherm at 129.1° C. (onset temperature) on the DSC curve were observed. Based on the low TGA weight loss and the only sharp DSC endotherm, Form D is postulated to be an anhydrate.

TABLE 6

XRPD Peak Search Report for Formula I, Form D

| Pos. [°2Th.] | Height [cts] | d-spacing [Å] | Rel. Int. [%] |
|---|---|---|---|
| 8.0 | 389 | 11.0 | 3.3 |
| 8.7 | 3614 | 10.2 | 30.3 |
| 9.2 | 603 | 9.6 | 5.1 |
| 9.8 | 1814 | 9.0 | 15.2 |
| 10.4 | 981 | 8.5 | 8.2 |
| 12.9 | 1805 | 6.9 | 15.1 |
| 13.4 | 2561 | 6.6 | 21.5 |
| 14.0 | 2422 | 6.3 | 20.3 |
| 14.8 | 11925 | 6.0 | 100.0 |
| 15.6 | 1044 | 5.7 | 8.8 |
| 16.4 | 1240 | 5.4 | 10.4 |
| 18.5 | 1595 | 4.8 | 13.4 |
| 19.7 | 3884 | 4.5 | 32.6 |
| 20.0 | 3839 | 4.4 | 32.2 |
| 20.8 | 2235 | 4.3 | 18.7 |
| 21.0 | 1286 | 4.2 | 10.8 |
| 23.1 | 1285 | 3.9 | 10.8 |
| 23.3 | 964 | 3.8 | 8.1 |
| 23.9 | 1354 | 3.7 | 11.4 |
| 25.5 | 1040 | 3.5 | 8.7 |
| 25.7 | 1104 | 3.5 | 9.3 |

Pharmaceutical Compositions and Formulations

A polymorph form of Formula I, may be formulated in accordance with standard pharmaceutical practice and according to procedures of Example 9, for use in therapeutic treatment (including prophylactic treatment) in mammals including humans. The present disclosure provides a pharmaceutical composition comprising the Formula I compound in association with one or more pharmaceutically acceptable carrier, glidant, diluent, or excipient.

Suitable carriers, diluents, glidants, and excipients are well known to those skilled in the art and include materials such as carbohydrates, waxes, water soluble and/or swellable polymers, hydrophilic or hydrophobic materials, gelatin, oils, solvents, water and the like.

The formulations may be prepared using conventional dissolution and mixing procedures. The compound of the present disclosure is typically formulated into pharmaceutical dosage forms to provide an easily controllable dosage of the drug and to enable patient compliance with the prescribed regimen.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

Pharmaceutical formulations of a polymorph form of Formula I compound may be prepared for various routes and types of administration with pharmaceutically acceptable diluents, carriers, excipients, glidants or stabilizers (Remington's Pharmaceutical Sciences (1995) 18th edition, Mack Publ. Co., Easton, Pa.), in the form of a lyophilized formulation, milled powder, or an aqueous solution. Formulation may be conducted by mixing at ambient temperature at the appropriate pH, and at the desired degree of purity, with physiologically acceptable carriers, i.e., carriers that are non-toxic to recipients at the dosages and concentrations employed. The pH of the formulation depends mainly on the particular use and the concentration of compound, but may range from about 3 to about 8.

The pharmaceutical formulation is preferably sterile. In particular, formulations to be used for in vivo administration must be sterile. Such sterilization is readily accomplished by filtration through sterile filtration membranes.

The pharmaceutical formulation ordinarily can be stored as a solid composition, a tablet, a pill, a capsule, a lyophilized formulation or as an aqueous solution.

The pharmaceutical formulations of the invention will be dosed and administered in a fashion, i.e., amounts, concentrations, schedules, course, vehicles and route of administration, consistent with good medical practice. Factors for consideration in this context include the particular disorder being treated, the clinical condition of the individual patient, the cause of the disorder, the site of delivery of the agent, the method of administration, the scheduling of administration, and other factors known to medical practitioners.

Acceptable diluents, carriers, excipients and stabilizers are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl, ethanol, or benzylalcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as lactose, sucrose, mannitol, trehalose or sorbitol; salt-forming counter-ions such as sodium; metal complexes (e.g., Zn-protein complexes); and/or non-ionic surfactants such as TWEEN™, including Tween 80, PLURONICS™ or polyethylene glycol (PEG), including PEG400. The active pharmaceutical ingredients may also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 18th edition, (1995) Mack Publ. Co., Easton, Pa. Other examples of drug formulations can be found in Liberman, H. A. and Lachman, L., Eds., Pharmaceutical Dosage Forms, Marcel Decker, Vol 3, $2^{nd}$ Ed., New York, N.Y.

Tablets may comprise one or more pharmaceutically acceptable carrier, glidant, diluent, or excipient selected from microcrystalline cellulose, lactose, sodium starch glycolate, and magnesium stearate.

Pharmaceutically acceptable glidants may be selected from silicon dioxide, powdered cellulose, microcrystalline cellulose, metallic stearates, sodium aluminosilicate, sodium benzoate, calcium carbonate, calcium silicate, corn starch, magnesium carbonate, asbestos free talc, stearowet C, starch, starch 1500, magnesium lauryl sulfate, magnesium oxide, and combinations thereof.

The pharmaceutical formulations include those suitable for the administration routes detailed herein. The formulations may conveniently be presented in unit dosage form and may be prepared by any of the methods well known in the art of pharmacy. Techniques and formulations generally are found in Remington's Pharmaceutical Sciences $18^{th}$ Ed. (1995) Mack Publishing Co., Easton, Pa. Such methods include the step of bringing into association the active ingredient with the carrier which constitutes one or more accessory ingredients. The formulations may be prepared by uniformly and intimately bringing into association the active ingredient with liquid carriers or finely divided solid carriers or both, and then, if necessary, shaping the product.

Pharmaceutical compositions may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may be a solution or a suspension in a non-toxic parenterally acceptable diluent or solvent, such as a solution in 1,3-butanediol or prepared from a lyophilized powder. Among the acceptable vehicles and solvents that may be employed are water, Ringer's solution and isotonic sodium chloride solution. In addition, sterile fixed oils may conventionally be employed as a solvent or suspending medium, including synthetic mono- or diglycerides. In addition, fatty acids such as oleic acid may likewise be used in the preparation of injectables.

In another aspect, the present disclosure relates to a method of treating a disease or condition mediated, at least in part, by leucine-rich repeat kinase 2 (LRRK2). In particular, the disclosure provides methods for preventing or treating a disorder associated with LRRK2 in a mammal, comprising the step of administering to said mammal a therapeutically effective amount of a compound provided herein. In some embodiments, the disease or condition mediated, at least in part, by LRRK2 is a neurodegenerative disease, for example, a central nervous system (CNS) disorder, such as Parkinson's disease (PD), Alzheimer's disease (AD), dementia (including Lewy body dementia and cascular dementia), amyotrophic lateral sclerosis (ALS), age related memory dysfunction, mild cognitive impairment (e.g., including the transition from mild cognitive impairment to Alzheimer's disease), argyrophilic grain disease, lysosomal disorders (for example, Niemann-PickType C disease, Gaucher disease) corticobasal degeneration, progressive supranuclear palsy, inherited frontotemporal dementia and parkinsonism linked to chromosome 17 (FTDP-17), withdrawal symptoms/relapse associated with drug addiction, L-Dopa induced dyskinesia, Huntington's disease (HD), and HIV-associated dementia (HAD). In other embodiments, the disorder is an ischemic disease of organs including but not limited to brain, heart, kidney, and liver.

In some other embodiments, the disease or condition mediated, at least in part, by LRRK2 is cancer. In certain specific embodiments, the cancer is thyroid, renal (including papillary renal), breast, lung, blood, and prostate cancers (e.g. solid tumor), leukemias (including acute myelogenous leukemia (AML)), or lymphomas. In some embodiments, the cancer is kidney cancer, breast cancer, prostate cancer, blood cancer, papillary cancer, lung cancer, acute myelogenous leukemia, or multiple myeloma.

In other embodiments, the presently disclosed compounds are used in methods for treatment of inflammatory disorders. In some embodiments, the disorder is an inflammatory disease of the intestines, such as Crohn's disease or ulcerative colitis (both generally known together as inflammatory bowel disease). In other embodiments, the inflammatory disease is leprosy, amyotrophic lateral sclerosis, rheumatoid arthritis, or ankylosing spondylitis. In some embodiments, the inflammatory disease is leprosy, Crohn's disease, inflammatory bowel disease, ulcerative colitis, amyotrophic lateral sclerosis, rheumatoid arthritis, or ankylosing spondylitis.

In other embodiments, the presently disclosed compounds are used in methods for treatment of multiple sclerosis, systemic lupus erythematosus, autoimmune hemolytic anemia, pure red cell aplasia, idiopathic thrombocytopenic purpura (ITP), Evans syndrome, vasculitis, bullous skin disorders, type 1 diabetes mellitus, Sjogren's syndrome, Devic's disease, and inflammatory myopathies.

EXAMPLES

Example 1 Isolation and Physicochemical Characteristics of Formula I Compound, 2-methyl-2-(3-methyl-4-(4-(methylamino)-5-(trifluoromethyl)pyrimidin-2-ylamino)-1H-pyrazol-1-yl)propanenitrile, CAS Reg. No. 1374828-69-9

Formula I compound, prepared according to Example 394 of U.S. Pat. No. 8,815,882, and Compound 12 of Estrada, A. A. et al (2013) J. Med. Chem. 57:921-936, each of which are specifically incorporated by reference, was dissolved in methyl tert-butylether (MTBE, 10 vol, 200 ml) to give a brown solution. This solution was filtered through 3M Zeta Plus activated carbon disc (R55SP, 5 cm diameter) at 3 ml/min. The filter was washed with MTBE (5 vol, 100 ml). The clear, not colored, solution (300 ml) was concentrated to 8 vol (160 ml) and charged into a 500 ml reactor. n-Heptane (8 vol, 160 ml) was added at 20° C. Solution initially remained clear but then crystallization started after 2 minutes. Temperature was increased gradually (rate 2° C./min). Full dissolution was achieved only at 69° C. Further heptane (4 vol, 80 ml) was added at 70° C.; clear solution was visually observed at 70° C. The temperature was set to 65° C. (1.0° C./min); At 65° C. with the clear solution, seed crystals of the Formula I compound (200 mg, same batch) were added and they did not dissolve. The temperature was then lowered to 20° C. over 8 hrs. It was stirred at 20° C. overnight. Solid was filtered and washed two times with the mother liquors. It was dried under vacuum at 40° C. for 2 hrs to give 15.91 g of crystalline Formula I compound (79.6% yield). Mother liquors were evaporated to dryness to give additional 3.47 g (17.4% recovery).

Example 2 Single Crystal Growth of Form C Polymorph

Block-like single crystals of the Formula I, Form C polymorph were obtained from n-butyl acetate/cyclohexane solvent mixture system (n-butyl acetate was the solvent while cyclohexane was the anti-solvent) via liquid vapor diffusion at RT. The experimental details are as follows.

Figure 14:
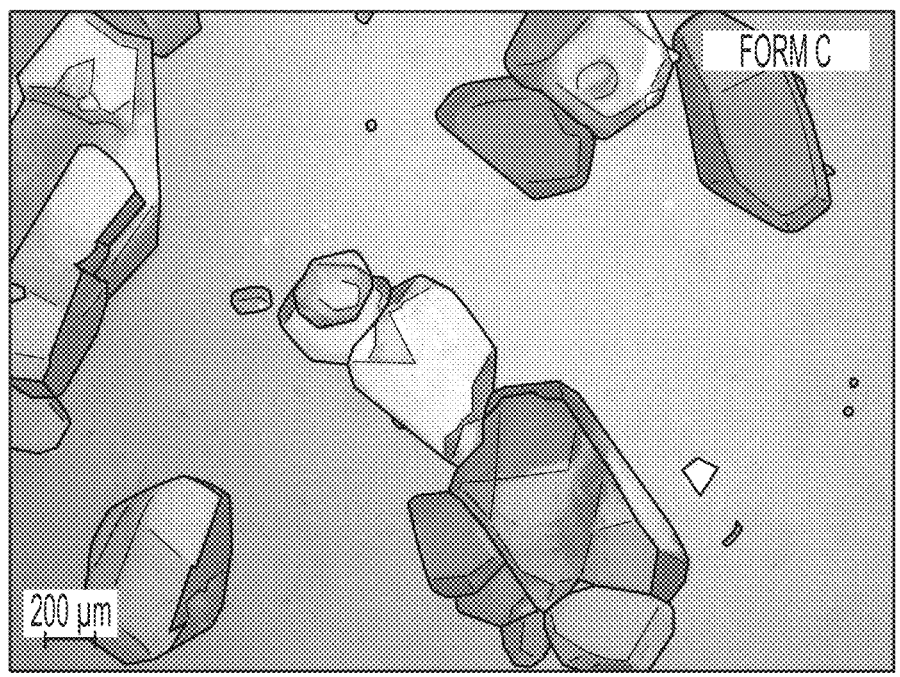
FIG. 14 shows a PLM image of Form C single crystals.

About 30 mg Formula I, Form A sample was weighed into a 3 mL glass vial with the addition of 65 μL n-butyl acetate solvent to dissolve all the solid sample. A small amount of the Form C crystal sample was also added into the 3-mL vial as the crystal seeds. Then the vial was added into a 20-mL glass vial with 4 mL anti-solvent cyclohexane in it for liquid-vapor diffusion at ambient temperature. After 11 days, block-like crystals were obtained as shown in FIG. 14.

Example 3 Single Crystal Growth of Form D Polymorph

Block-like single crystals of the Formula I, Form D polymorph were obtained from acetone/n-heptane (1:10, v/v) solvent mixture system via slow evaporation at RT. The experimental details are as follows.

Figure 15:
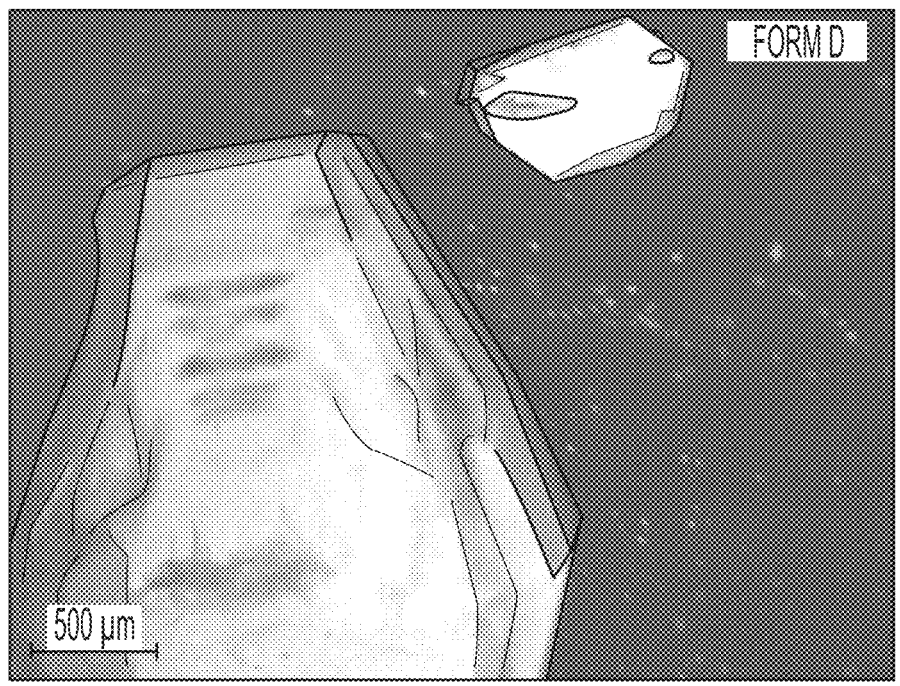
FIG. 15 shows a PLM image of Form D single crystals.

About 30 mg Formula I, Form A sample was weighed into a 4 mL shell vial (44.6 mm×14.65 mm) with the addition of 0.2 mL n-butyl acetate and 2.0 mL n-heptane to dissolve the solid sample. A small amount of the Form D crystal sample was also added into the 4-mL vial as the crystal seeds. Then the vial was placed in the fume hood for slow evaporation at ambient temperature. After 15 days, block-like crystals were obtained as shown in FIG. 15.

Example 4 Single Crystal Structure Determination

Colorless block-like single crystals were selected from the Form C single crystals sample or Form D single crystals sample and wrapped with Paratone-N (an oil based cryoprotectant). The crystals were mounted on a mylar loop in a random orientation and immersed in a stream of nitrogen at 150 K. Preliminary examination and data collection were performed on an Agilent SuperNova® (Cu/K$_\alpha$ λ=1.54178 Å) diffractometer and analyzed with the CrysAlisPro® (Agilent, Version:1.171.38.41) software package.

The data collection details of Form C single crystal are as follows: Cell parameters and an orientation matrix for data collection were retrieved and refined by CrysAlisPro® software using the setting angles of 6568 reflections in the range 4.0790°<θ<70.0660°. The data were collected to a maximum diffraction angle (θ) of 70.266° at 150.2(2) K. The data set was 99.9% complete having a Mean I/σ of 19.4 and D min (Cu) of 0.82 Å.

The data reduction details of Form C single crystal as follows: Frames were integrated with CrysAlisPro®, Version:1.171.38.41 software. A total of 12836 reflections were collected, of which 6205 were unique. Lorentz and polarization corrections were applied to the data. An empirical absorption correction was performed using spherical harmonics, implemented in SCALE3 ABSPACK scaling algorithm. The absorption coefficient μ of this material is 0.964 mm$^{-1}$ at this wavelength (λ=1.54178 Å) and the minimum and maximum transmissions are 0.80956 and 1.00000. Intensities of equivalent reflections were averaged. The agreement factor for the averaging was 2.08% based on intensity.

The structure of Form C was solved in the space group C2/c by Direct Methods using the ShelXS™ structure solution program (Sheldrick, G. M. (2008). Acta Cryst. A64: 112-122) and refined with ShelXS™, Version 2014/7 refinement package using full-matrix least-squares on F$^2$ contained in OLEX2 (Dolomanov, O. V., et al, (2009) J. Appl. Cryst. 42:339-341). All non-hydrogen atoms were refined anisotropically. The positions of hydrogen atoms occur on carbon atoms were calculated geometrically and refined using the riding model, but the hydrogen atoms occur on nitrogen atoms were refined freely according to the Fourier Maps.

The data collection details of Form D single crystal are as follows: Cell parameters and an orientation matrix for data collection were retrieved and refined by CrysAlisPro® software using the setting angles of 30349 reflections in the range 4.0180°<θ<70.5190°. The data were collected to a maximum diffraction angle (θ) of 70.562° at 150 K. The data set was 89.9% complete having a Mean I/σ of 29.3 and D min (Cu) of 0.82 Å.

The data reduction details of Form D single crystal are as follows: Frames were integrated with CrysAlisPro®, Version:1.171.38.41 software. A total of 47670 reflections were collected, of which 11179 were unique. Lorentz and polarization corrections were applied to the data. An empirical absorption correction was performed using spherical harmonics, implemented in SCALE3 ABSPACK scaling algorithm. The absorption coefficient μ of this material is 0.980 $mm^{-1}$ at this wavelength (λ=1.54178 Å) and the minimum and maximum transmissions are 0.83622 and 1.00000. Intensities of equivalent reflections were averaged. The agreement factor for the averaging was 2.69% based on intensity.

The structure of Form D was solved in the space group $Pca2_1$ by Direct Methods using the ShelXS structure solution program and refined with ShelXS™, Version 2014/7 refinement package using full-matrix least-squares on $F^2$ contained in OLEX2. All non-hydrogen atoms were refined anisotropically. Hydrogen atom positions were calculated geometrically and refined using the riding model.

TABLE 7

| Single-crystal X-ray diffraction (SCXRD) instrument parameters | |
|---|---|
| Instrument | Agilent SuperNova |
| X-Ray sources generator | SuperNova Microfocus X-ray Source ($Cu/K_α$: 1.54184 Å) 50 KV, 0.8 mA |
| Detector | Eos CCD detector (Detector resolution: 16.0450 pixels $mm^{-1}$) |
| Goniometer | Four-circle Kappa Goniometer |
| Low Temperature Devices | Oxford Cryosystems |
| Software | CrysAlisPro (Version: 1.171.38.41) |

Polymorph forms of the Formula I compound were solved using the ShelXT (Sheldrick, G. M. (2015). Acta Cryst. A71, 3-8) structure solution program (Intrinsic Phasing method) and refined using SHELXL-2015 refinement package (Sheldrick, G. M. (2015). Acta Cryst. A71, 3-8)) (full-matrix least-squares on $F^2$) contained in OLEX2 (Dolomanov, O. V. et al, "OLEX2: a complete structure solution, refinement and analysis program". J. Appl. Cryst. 2009, 42, 339-341). The calculated XRPD pattern was obtained from Mercury (Macrae, C. F., et al, Appl. Cryst. (2006) 39:453-457) and the crystal structure representations were generated by Diamond. The single crystal X-ray diffraction data was collected at 296 K using Bruker D8 VENTURE diffractometer (Mo/Kα radiation, λ=0.71073 Å). Table 8 shows the crystallographic data and structure refinement of Forms A, C, and D.

TABLE 8

Crystallographic data and structure refinement of Formula I single crystal polymorph Forms A, C, D

| Parameters | Form A | Form C | Form D |
|---|---|---|---|
| Empirical formula | $C_{14}H_{16}F_3N_7$ | $C_{14}H_{16}F_3N_7$ | $C_{14}H_{16}F_3N_7$ |
| Formula weight | 339.34 | 339.34 | 339.34 |
| Temperature | 296 K | 150.2(2) K | 150 K |
| Wavelength | Mo/Kα (λ = 0.71073 Å) | Cu/$K_α$ (λ = 1.54178 Å) | Cu/Kα (λ = 1.54178 Å) |
| Crystal system, space group | Monoclinic, $P2_1/n$ | Monoclinic, C2/c | Orthorhombic, $Pca2_1$ |
| Unit cell dimensions | a = 5.325(2) Å<br>b = 13.005(5) Å<br>c = 24.778(9) Å<br>α = 90°<br>β = 94.408(11)°<br>γ = 90° | a = 13.7032(3) Å<br>b = 17.5697(4) Å<br>c = 27.4196(6) Å<br>α = 90°<br>β = 91.982(2)°<br>γ = 90° | a = 17.63410(10) Å<br>b = 14.03430(10) Å<br>c = 26.2102(2) Å<br>a = 90°<br>β = 90°<br>γ = 90° |
| Volume | 1710.7(11) $Å^3$ | 6597.6(3) $Å^3$ | 6486.56(8) $Å^3$ |
| Z, Calculated density | 4, 1.318 g/$cm^3$ | 16, 1.367 g/$cm^3$ | 16, 1.390 g/$cm^3$ |
| Absorption coefficient | 0.108 $mm^{-1}$ | 0.964 $mm^{-1}$ | 0.980 $mm^{-1}$ |
| F(000) | 704.0 | 2816.0 | 2816.0 |
| Crystal size | 0.6 × 0.5 × 0.2 $mm^3$ | 0.4 × 0.4 × 0.3 $mm^3$ | 0.6 × 0.5 × 0.2 $mm^3$ |
| 2 Theta range for data collection | 4.548° to 57.89° | 6.45° to 140.532° | 6.744° to 141.124° |
| Limiting indices | −6 ≤ h ≤ 6<br>−16 ≤ k ≤ 16<br>−32 ≤ l ≤ 33 | −13 ≤ h ≤ 16<br>−21 ≤ k ≤ 15<br>−31 ≤ l ≤ 33 | −21 ≤ h ≤ 21<br>−16 ≤ k ≤ 14<br>−23 ≤ l ≤ 31 |
| Reflections collected/Independent reflections | 28803/3825 [R(int) = 0.0509] | 12836/6205 [$R_{int}$ = 0.0208, $R_{sigma}$ = 0.0267] | 47670/11179 [$R_{int}$ = 0.0269, $R_{sigma}$ = 0.0214] |
| Completeness | 84.57% | 98.24% | 89.80% |
| Refinement method | Full-matrix least-squares on $F^2$ | Full-matrix least-squares on $F^2$ | Full-matrix least-squares on $F^2$ |
| Data/restraints/parameters | 3825/0/221 | 6205/0/441 | 11179/1/881 |
| Goodness-of-fit on $F^2$ | 1.081 | 1.038 | 1.031 |
| Final R indices [I > 2sigma(I)] | $R_1$ = 0.0993, $wR_2$ = 0.2464 | $R_1$ = 0.0461, $wR_2$ = 0.1241 | $R_1$ = 0.0320, $wR_2$ = 0.0857 |
| Final R indexes [all data] | | $R_1$ = 0.0518, $wR_2$ = 0.1281 | $R_1$ = 0.0339, $wR_2$ = 0.0872 |
| Largest diff. peak and hole | 0.74/−0.78 e.$Å^{-3}$ | 0.85/−0.37 e.$Å^{-3}$ | 0.19/−0.21 e.$Å^{-3}$ |

Single crystals of Form C and Form D were prepared and analyzed by single crystal X-ray diffraction (SCXRD). The single crystal structures of Form C and Form D were determined successfully.

The SCXRD characterization confirmed that Form C crystallized in monoclinic crystal system and C2/c space group with the unit cell parameters {a=13.7032(3) Å, b=17.5697(4) Å, c=27.4196(6) Å; α=90°, β=91.982 (2)°, γ=90°}. The cell volume V was calculated to be 6597.6(3) Å$^3$. The asymmetric unit is comprised of two molecules, indicating that Form C is an anhydrate. The calculated density of Form C is 1.367 g/cm$^3$. The unit cell of the single crystal is comprised of sixteen molecules.

The SCXRD characterization confirmed that Form D crystallized in orthorhombic crystal system and Pca2$_1$ space group with unit cell parameters {a=17.63410(10) Å, b=14.03430(10) Å, c=26.2102(2) Å; α=90°, β=90°, γ=90°}. The cell volume V was calculated to be 6486.56(8) Å$^3$. The asymmetric unit is comprised of four molecules, indicating that Form D is an anhydrate. The calculated density of Form D is 1.390 g/cm$^3$. The unit cell of the single crystal is comprised of sixteen molecules.

Example 5 Polarized Light Microscopy (PLM)

PLM images were captured using Axio Lab.A1 upright microscope with ProgRes® CT3 camera at RT.

Example 6 Ambient X-Ray Powder Diffractometry (XRPD)

XRPD patterns were collected with a PANalytical Empyrean X-ray powder diffract meter was used with XRPD parameters of Table 9:

TABLE 9

| XRPD instrument parameters | | |
|---|---|---|
| Parameters | Empyrean | X' Pert3 |
| X-Ray wavelength | Cu, kα; Kα1 (Å): 1.540598 Kα2 (Å): 1.544426 intensity ratio Kα2/Kα1: 0.50 | Cu, kα; Kα1 (Å): 1.540598 Kα2 (Å): 1.544426 intensity ratio Kα2/Kα1: 0.50 |
| X-Ray tube setting | 45 kV, 40 mA | 45 kV, 40 mA |
| Divergence slit | Automatic | Automatic |
| Scan mode | Continuous | Continuous |
| Scan range (°2TH) | 3°~40° | 3°~40° |
| Step size (°2TH) | 0.0167 | 0.0263 |
| Scan step time (s) | 18 | 50 |
| Test time (s) | 5 min 30 s | 5 min 04 s |

Example 7 TGA and DSC Test

TGA data were collected using a TA Q500/Q5000 TGA from TA Instruments. DSC was performed using a TA Q200/Q2000 DSC from TA Instruments. Detailed parameters used are listed in Table 10:

TABLE 10

| TGA and DSC parameters | | |
|---|---|---|
| Parameters | TGA | DSC |
| Method | Ramp | Ramp |
| Sample pan | Platinum, open | Aluminum, crimped |
| Temperature | RT-desired temperature | 25° C.-desired temperature |

TABLE 10-continued

| TGA and DSC parameters | | |
|---|---|---|
| Parameters | TGA | DSC |
| Heating rate | 10° C./min | 10° C./min |
| Purge gas | N$_2$ | N$_2$ |

Example 8 DVS Test

DVS was measured via a SMS (Surface Measurement Systems) DVS Intrinsic. The relative humidity at 25° C. were calibrated against deliquescence points of LiCl, Mg(NO$_3$)$_2$ and KCl. Parameters for DVS test were listed in Table 11.

TABLE 11

| DVS parameters | |
|---|---|
| Parameters | DVS |
| Temperature | 25 C. |
| Sample size | 10-20 mg |
| Gas and flow rate | N2, 200 ml/min |
| dm/dt | 0.002%/min |
| Min. Dm/dtstability duration | 10 min |
| Max. equilibrium time | 180 min |
| RH range | 0% RH to 95% RH |
| RH step size | 10% RH from 0-90% RH, then 5% RH from 90-95% RH |

Example 9 Formulation of Crystalline Formula I Compound

After crystallization, polymorph forms of Formula I compound, may be formulated by dry granulation using a roller compactor, followed by a tableting operation. Additional ingredients in the tablets may include microcrystalline cellulose (Avicel® PH, FMC BioPolymer), lactose (FastFlo®, Foremost Farms USA), sodium starch glycolate (EXPLOTAB®, JRS Pharma), or magnesium stearate (Hyqual®, Macron Fine Chemicals).

Example 10 Amorphous Form E

Figure 16:
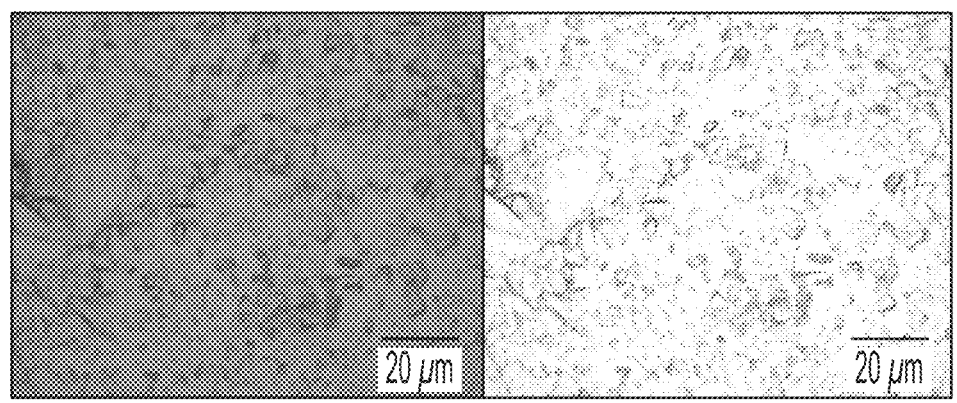
FIG. 16 shows polarized light microscopy images of amorphous Form E.
Figure 17:
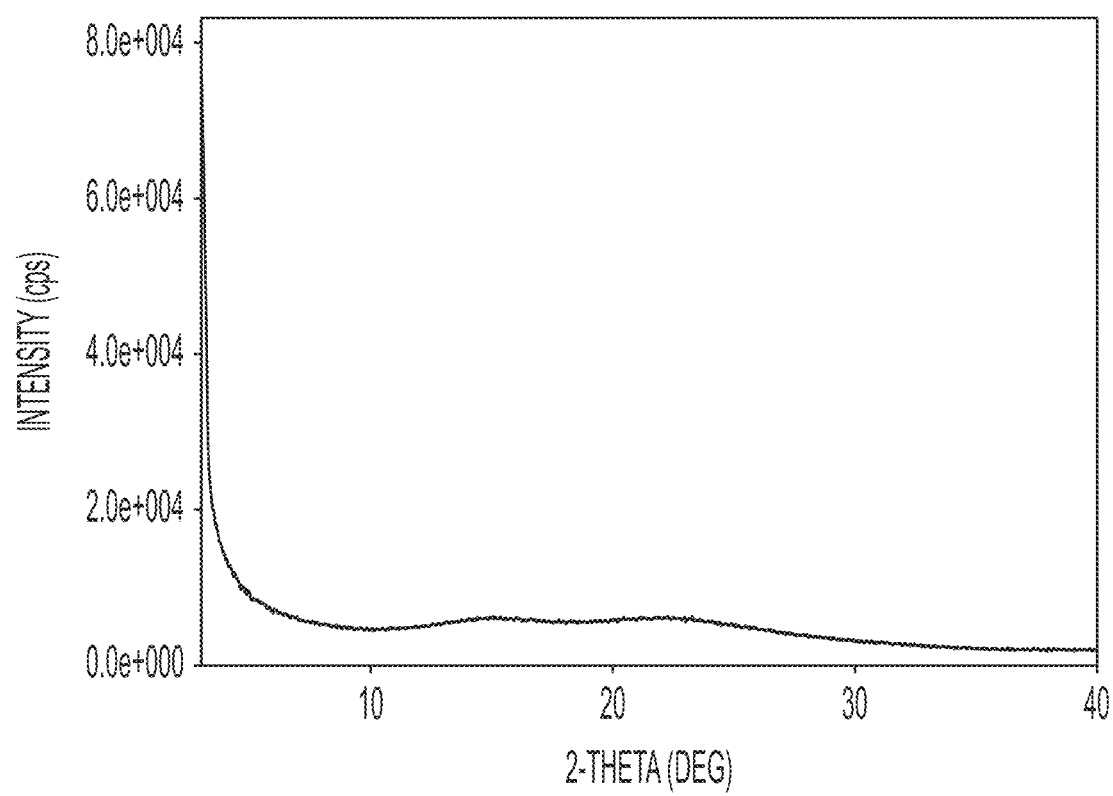
FIG. 17 shows XRPD Diffractogram of amorphous Form E.

A 0.5 g sample of solid 2-methyl-2-(3-methyl-4-(4-(methylamino)-5-(trifluoromethyl)pyrimidin-2-ylamino)-1H-pyrazol-1-yl)propanenitrile was warmed until liquid was observed and then added to a vial cooled to −45° C. resulting in a "glass" solid. By polarized light microscopy (PLM), no birefringence was observed (FIG. 16). Analysis by XRPD shows no inflection peaks and shows a characteristic "halo" indicating an amorphous solid (FIG. 17). Thermal analysis by DSC shows an exothermic crystallization event with an onset at 77.8° C., followed by a broad endothermic melt indicating a crystalline melt with an onset at 122.8° C.

Although the foregoing invention has been described in some detail by way of illustration and example for purposes of clarity of understanding, the descriptions and examples should not be construed as limiting the scope of the invention. Accordingly, all suitable modifications and equivalents may be considered to fall within the scope of the invention as defined by the claims that follow. The disclosures of all patent and scientific literature cited herein are expressly incorporated in their entirety by reference.

What is claimed is:

1. An amorphous compound, 2-methyl-2-(3-methyl-4-(4-(methylamino)-5-(trifluoromethyl)pyrimidin-2-ylamino)-1H-pyrazol-1-yl)propanenitrile.

2. A pharmaceutical composition comprising the amorphous compound of claim 1 and a pharmaceutically acceptable excipient.

* * * * *